United States Patent [19]

Trevino et al.

[11] Patent Number: 5,733,526
[45] Date of Patent: Mar. 31, 1998

[54] HYDROCARBON OIL/FLUOROCHEMICAL PREPARATIONS AND METHODS OF USE

[75] Inventors: Leo A. Trevino, San Diego, Calif.; Jean G. Riess, Falicon, France; Luis A. Dellamary, San Marcos, Calif.; Marie-Pierre Krafft, Nice, France; Thomas E. Tarara, San Diego, Calif.

[73] Assignee: Alliance Pharmaceutical Corp., San Diego, Calif.

[21] Appl. No.: 572,859

[22] Filed: Dec. 14, 1995

[51] Int. Cl.$^6$ ............................ A61K 49/04; A61K 31/03
[52] U.S. Cl. .................. 424/9.52; 424/9.5; 424/455; 514/937; 514/749
[58] Field of Search ........................ 424/9.5, 9.51, 424/9.52, 9.1, 455, 450; 514/937, 938, 749; 252/302, 350

[56] References Cited

U.S. PATENT DOCUMENTS

| | | |
|---|---|---|
| 3,975,512 | 8/1976 | Long, Jr. . |
| 5,114,703 | 5/1992 | Wolf et al. . |
| 5,514,720 | 5/1996 | Clark et al. ........................ 514/749 |

FOREIGN PATENT DOCUMENTS

| | | | |
|---|---|---|---|
| 0220153A1 | 4/1987 | European Pat. Off. . | |
| 9301798 | 2/1993 | WIPO ................... | A61K 9/00 |
| 9414415 | 7/1994 | WIPO . | |

OTHER PUBLICATIONS

Solé-Violan et al., "Partition Coefficients of Mixed Fluorocarbon–Hydrocarbon Compounds Between Fluorocarbons and Hexadecane", New. J. Chem., 17, pp. 581–583, 1993.

Cecutti, et al. "New Formulation of Blood Substitutes: Optimization of Novel Fluorinated Microemulsions" Eur. J. Med. Chem. 24:485–492 (1989).

Clary, et al. "Synthesis and Evaluation of the In Vivo Tolerance of Amido Fluorocarbon/Fluorocarbon and Fluorocarbon/Hydrocarbon Double–Chain Phosphocholines Deriving from Diaminopropanols and Serine" Tetrahedron 51(47):13073–13088 (1995).

Gaines, George L. "Surface Activity of Semifluorinated Alkanes: F(CF$_2$)m(CH$_2$)n H" Langmuir 7:3054–3056 (1991).

Greiner, et al. "Fluorinated Surfactants Intended for Biomedical Uses" *Organofluorine Compounds in Medicinal Chemistry and Biomedical Applications* Filler, et al. eds. pp. 339–380, Elsevier Science Publishers (1993).

Hageluken, et al. "Lipophilic β–Adrenoceptor Antagonists and Local Anesthetics Are Effective Direct Activators of G–Proteins" Biochem. Pharm. 47(10):1789–1795 (1994).

Hopken, J. "Fluorocarbon–Hydrocarbon Molecules" Thesis from University of Twente, Enschede, The Netherlands (1991).

Hopken, et al. "Melting, Crystallization, and Solution Behavior of Chain Molecules with Hydrocarbon and Flurocarbon Segments" Makromol. Chem. 189:911–925 (1988).

Hopken, et al. "Self–Organization of Amphiphilic Fluorocarbon–Hydrocarbon Molecules–I. Synthesis and Interfacial Activity of Allyl Ethers" New Polymeric Mater. 2(4):339–356 (1991).

Hughes, et al. "Effect of Acylation on the Ocular Disposition of Acyclovir II: Corneal Permeability and Anti–HSV 1 Activity of 2'–Esters in Rabbit Epithelial Keratitis" J. of Ocular Pharm. 9(4):299–309 (1993).

Lo Nostro, et al. "Aggregation of a Semifluorinated n–Alkane in Perfluorooctane" J. Phys. Chem. 97:6535–6540 (1993).

Meinert, et al. "Synthesis, Interfacial Active Properties and Toxicity of New Perfluoroalkylated Surfactants" Biomat. Art. Cells & Immob. Biotech. 20(1):115–124 (1992).

Meinert, et al. "The Use of Semifluorinated Alkanes in Blood–Substitutes" Biomat. Art. Cells & Immob. Biotech. 21(5):583–595 (1993).

Meinert, et al. "Semifluorinated Symmetrical Diethers" J. of Fluorine Chem. 68:221–226 (1994).

Moriguchi, et al. "Simple Method of Calculating Octanol/Water Partition Coefficient" Chem. Pharm. Bull. 40(1):127–130 (1992).

Morita, et al. "Interfacial Properties and Emulsion Stability in Fluorinated Oil–Non–Fluorinated Oil–Surfactant(s) Systems" Collids and Surfaces 67:81–93 (1992).

Pugh, et al. "Amphiphilic Molecules with Hydrocarbon and Fluorocarbon Segments" Polym. Prep. 29(1):460–461(1988).

Russell, et al. "Structural Characterization of Semifluorinated n–Alkanes. 2. Solid–Solid Transition Behavior" Macromolecules 19:1135–1143 (1986).

Tang–Liu, et al. "Lenticular Uptake and Distribution of Xenobiotics and Amino Acids" J. of Ocular Pharm. 8(3):267–277 (1992).

Turberg, et al. "Semifluorinated Hydrocarbons: Primitive Surfactant Molecules" J. Am. Chem. Soc. 110:7797–7801 (1988).

Twieg, et al. "Melt Properties of Ring Polystyrenes" Macromolecules 18:1359–1361 (1985).

Viney, et al. "Transitions to Liquid Crystalline Phases in a Semifluorinated Alkane" Mol. Cryst. Liq. Cryst. 168:63–82 (1989).

Yokogawa, et al. "Relationships in the Structure– Tissue Distribution of Basic Drugs in the Rabbit" Pharmaceutical Res. 7(7):691–696 (1990).

*Primary Examiner*—Gary E. Hollinden
*Assistant Examiner*—Michael G. Hartley
*Attorney, Agent, or Firm*—Knobbe, Martens Olson & Bear, LLP

[57] ABSTRACT

Novel hydrocarbon oil/fluorochemical preparations and methods for their use are provided. The preparations, which preferably comprise a fluorophilic dispersing agent, may be in the form of hydrocarbon oil-in-fluorochemical dispersions or in the form of a multiple emulsion comprising a polar liquid continuous phase and are particularly useful for administering bioactive agents. In particular the preparations of the present invention may be used to control the bioavailability and improve the efficacy of lipophilic bioactive agents having limited solubility in an aqueous physiological environment.

41 Claims, 4 Drawing Sheets

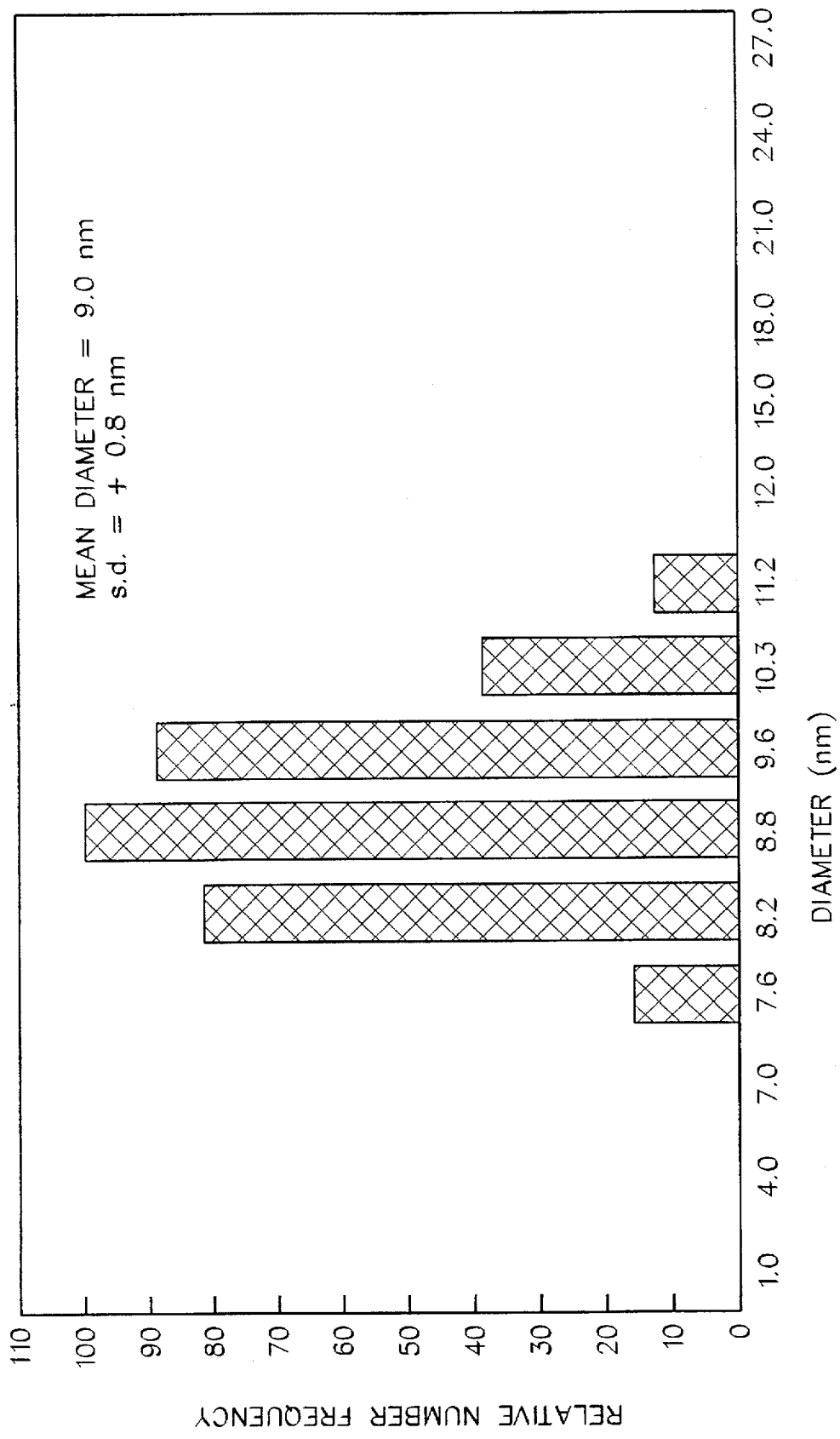

HYDROCARBON OIL/FLUOROCHEMICAL PREPARATIONS AND METHODS OF USE

FIELD OF THE INVENTION

In a broad aspect the present invention generally relates to novel hydrocarbon oil/fluorochemical preparations that may be used to administer bioactive agents. More particularly, preferred embodiments of the invention are directed to hydrocarbon oil-in-fluorochemical dispersions and hydrocarbon oil-in-fluorochemical-in-water emulsions that may be used to control the bioavailability and efficacy of lipophilic compounds having limited solubility in an aqueous physiologic environment.

BACKGROUND OF THE INVENTION

The efficacy of many bioactive agents is predicated on their ability to proceed to the selected target sites and remain present in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes that are subject to repeated drainage or flushing as part of the body's natural physiological functions offers significant impediments to the effective administration and controlled release of bioactive agents. In this respect, delivery and retention problems are often encountered when administering compounds through the respiratory or gastrointestinal tracts. Repeated administration of fairly large doses are often required to compensate for the amount of drug washed away and to maintain an effective dosing regimen when employing such routes. Moreover, the molecular properties of the bioactive compound may impair the absorption through a given delivery route, thereby resulting in a substantial reduction in efficacy. This is particularly true of lipophilic compounds that are not soluble in aqueous environments. For instance, insoluble particulates are known to be subject to phagocytosis and pinocytosis, resulting in the accelerated removal of the compound from the target site. Such reductions in delivery and retention time complicate dosing regimes, waste bioactive resources and generally reduce the overall efficacy of the administered drug.

Unlike many hydrophilic compounds, the delivery of lipid soluble or lipophilic drugs by conventional means has been and continues to be problematic. Unfortunately, a number of the most promising therapeutic and diagnostic agents currently under development are relatively insoluble in water. Some are bulky polycyclic molecules whose substantial physical size, coupled with the intrinsic lipophilicity of their molecular structure, has severely limited their use in practical bioactive applications. For instance, the oral administration of lipophilic agents using conventional tablets and capsules suffers the disadvantage of a variable rate of absorption and depends on factors such as the presence or absence of food, the pH of gastrointestinal fluids and gastric emptying rates. Moreover, the degradation of labile drugs by gastric fluids and drug metabolizing enzymes may reduce the drug bioavailability to the point of therapeutic failure.

Other delivery routes fare little better when lipophilic compounds are administered using conventional delivery vehicles. Administration of these water insoluble drugs often requires that they be formulated in the form of hydrocarbon oil in water emulsions or that they be solubilized into a water miscible phase. This suffers drawbacks associated with the formulation of a suitably stable dosage form. For example, the current method used for the intravenous administration of the highly lipophilic cancer drug Taxol involves the use of a polyoxyethylated castor oil vehicle that has been associated with hypersensitivity reactions including dyspnea, bronchospasm, urticaria, and hypotension. In addition, the intravenous administration of drugs such as Taxol, which exhibit high systemic toxicities, severely limits their therapeutic capacity. Thus, despite encouraging results with existing delivery systems, the inherently low bioavailability of these lipophilic compounds at the target site due to inefficient or toxic delivery systems substantially reduces their efficacy.

In spite of the difficulties associated with the delivery of lipophilic drugs, the potential advantages in developing methods to do so are great. Extensive work has been done to show that the membrane permeability, bioavailability and efficacy of drugs often increases with increasing lipophilicity. The development of new systems for the delivery and prolonged release of these compounds could, therefore, significantly increase the therapeutic efficacies for the treatment of a wide variety of indications.

In this respect, one class of delivery vehicles that has shown great promise when used for the administration of bioactive agents is fluorochemicals. During recent years, fluorochemicals have found wide ranging application in the medical field as therapeutic agents. The use of fluorochemicals to treat medical conditions is based, to a large extent, on the unique physical and chemical properties of these substances. In particular, the relatively low reactivity of fluorochemicals allows them to be combined with a wide variety of compounds without altering the properties of the incorporated agent. This relative inactivity, when coupled with other beneficial characteristics such as an ability to carry substantial amounts of oxygen, radioopaqueness for certain fluorochemicals and forms of radiation as well as low surface energies, have made fluorochemicals invaluable for a number of therapeutic and diagnostic applications.

For example, various fluorochemical emulsions have been used as oxygen carriers during medical procedures. Conventional fluorochemical-in-water emulsions, which may be infused directly into the blood stream, consist of a selected fluorochemical dispersed in the form of droplets in a continuous aqueous phase. Because of the high oxygen-carrying capacity of fluorochemicals, such emulsions are particularly useful as blood substitutes to provide oxygen to the vascular system. Fluosol® (Green Cross Corp., Osaka, Japan), a formerly commercially available emulsion containing fluorochemicals, has been used as a gas carrier to oxygenate the myocardium during percutaneous transluminai coronary angioplasty. Fluorochemicals have also been used as contrast enhancement media in radiological imaging (U.S. Pat. No. 3,975,512) and in nuclear magnetic resonance imaging (U.S. Pat. No. 5,114,703). A fluorochemical emulsion is currently being investigated as a means of expanding the efficacy of perioperative hemodilution and reducing the need for homologous blood transfusion. Other proposed medical uses include the treatment of cardiovascular and cerebrovascular diseases, organ preservation and cancer therapy; diagnostic ultrasound imaging and veterinary therapy.

In addition to traditional fluorochemical-in-water emulsions, other fluorochemical systems have been examined for utility under a variety of conditions. For example, it has been shown that water-in-fluorochemical reverse emulsions may be stabilized through the selection of appropriate emulsifiers and used as drug delivery vehicles. It has also been demonstrated that hydrocarbon liquids and fluorocarbon liquids may be used to form relatively stable systems. Such systems have been reported as being useful. In particular, various compounds have been shown to exhibit amphiphilic behavior when mixed with both hydrocarbon and fluorochemical liquids in the absence of water. (Meinert, H., Geister, U., J. Fluorine Chem. (1984), 68(2) 221; Turberg, M. P. and Brady, J. E., J. Am. Chem. Soc., 1988, 110, 7797; Höpken, J., Pugh, C., Richtering, W., and Möller, M., Makromol. Chem., 1988, 189, 911; Höpken, J., Möller, M. and Boileau, S., New Polymeric Mater., 1991, 2, 339; Twieg, R. J., Russell, T. P., Siemens, R. and Rabolt, J. F., Macromolecules, 1985, 1361; Höpken, J., Ph.D. Thesis, University of Twente, Enschede, The Netherlands, 1991). For example, Japanese patent application 86-135852 describes a hair conditioning emulsion comprising a perfluorocarbon dispersed in a hydrocarbon. However, while the possibility of such hydrocarbon-fluorochemical systems has been demonstrated, there is no indication that they may be used for the delivery of pharmaceutical compounds.

Accordingly, despite the preparation of a number of fluorochemical systems, the administration of bioactive compounds, particularly therapeutics designed for absorption by the body, still presents a number of difficulties. A significant problem associated with conventional fluorochemical mediated drug delivery is that the large majority of drugs (lipophilic or hydrophilic) are relatively insoluble in neat fluorochemicals or in the fluorochemical phase of traditional emulsions. As such, preparation of crude dispersions of an insoluble pharmaceutical agent in a neat fluorochemical carrier or emulsion. These formulations may present issues involving administration of the compound including stability, particle size, dose reliability, emulsion consistency and, ultimately, bioavailability. As a consequence of the heterogeneity of these systems, dispersions of solid particulates may not provide for the delivery of drugs in a uniform and reproducible manner.

In view of such limitations, the ability to use substantially homogeneous fluorochemical or fluorochemical based preparations, to reliably deliver effective amounts of bioactive agents, either in conjunction with fluorochemical mediated therapy or in a separate dosing regime, would be of great benefit. The use of such fluorochemical drug delivery vehicles would be particularly favorable for lipophilic drugs that present special problems in an aqueous physiological environment.

Accordingly, it is an object of the present invention to provide fluorochemical preparations, including dispersions and multiple emulsions incorporating therapeutic or diagnostic compounds which exhibit improved shelf-lives and stability.

It is a further objective of the present invention to provide bioactive preparations capable of effectively delivering lipophilic bioactive agents and allowing improved control over drug release.

It is yet a further objective of the present invention to provide a method for the formation of new preparations including dispersions, microemulsions and multiple emulsions comprising bioactive agents exhibiting enhanced bioavailability.

SUMMARY OF THE INVENTION

The present invention accomplishes these and other objectives by providing unique hydrocarbon oil/fluorochemical preparations ("HO/FC preparations") which may be used for the administration of bioactive agents. In preferred embodiments the invention comprises hydrocarbon oil-in-fluorochemical (HO/FC) dispersions comprising a fluorophilic dispersing agent. While hydrocarbon oils compatible with the present invention have advantageous drug delivery or inherent pharmaceutical properties, they are generally not miscible with the disclosed fluorochemicals. Yet, it has been unexpectedly discovered that, in the presence of selected fluorophilic dispersing agents, unique, substantially homogeneous, hydrocarbon oil/fluorochemical preparations could be formed. Preferably, this fluorophilic dispersing agent is selected from the group consisting of fluorinated surfactants and fluorocarbon-hydrocarbon diblock molecules. Moreover, it was further discovered that the stabilized HO/FC dispersions may be combined with a polar liquid and an emulsifying agent to provide unique hydrocarbon oil-in-fluorochemical-in-polar liquid multiple emulsions (HO/FC/W) having a disperse phase (or "HO/FC disperse phase") and a continuous polar liquid phase. Both the HO/FC dispersions and the HO/FC/W multiple emulsions may comprise a bioactive hydrocarbon oil or may be combined with bioactive agents to provide stable bioactive preparations having extended shelf-lives, enhanced bioavailability and prolonged delivery profiles.

In one embodiment of the invention a hydrocarbon oil-in-fluorochemical dispersion comprising at least one hydrocarbon oil, at least one fluorochemical and an effective dispersing mount of at least one fluorophilic dispersing agent is provided. Preferably, the preparations comprise a dispersed hydrocarbon oil phase and a continuous fluorochemical phase. By "effective dispersing amount" it is meant the amount of fluorophilic dispersing agent required to provide a substantially homogeneous preparation. Those skilled in the art will appreciate that the "effective dispersing amount" of a fluorophilic agent will vary depending on such factors as the choice of components and their concentrations as well as the actual fluorophilic dispersing agent selected. In preferred embodiments the dispersion comprises from about 0.01% to about 75% (v/v) of at least one hydrocarbon oil, 25% to about 99.9% (v/v) of at least one fluorochemical, and 0.01% to about 99% (v/v) of at least one fluorophilic dispersing agent. Other additives, including those that contribute to stability, drug solubility and control of drug delivery profiles, may also be incorporated in the HO/FC dispersions of the present invention.

A wide variety of hydrocarbon oils and hydrocarbon oil derivatives may be used to form the preparations of the present invention. As used herein, the term "hydrocarbon oil" is held to mean any compound, including bioactive agents, which are capable of being solubilized in the fluorochemical phase using dispersing agents disclosed herein. That is, the hydrocarbon oil itself may be a bioactive agent or drug although non-bioactive hydrocarbon oils are compatible as well. In any case, the selected hydrocarbon oil is preferably biocompatible and readily available from natural or synthetic sources. Hydrocarbon oils compatible with the present invention include saturated or unsaturated hydrocarbons (cyclic, aliphatic or aromatic), or hydrocarbon derivatives including substituted and unsubstituted compounds (e.g. alcohols, aldehydes, ketones, amines, ethers, amides, etc.). Lipophilic bioactive compounds that are solubilizable using the disclosed dispersing agents, such as selected steroidal compounds, aminoglycosidic compounds and cholesterol derivatives are also hydrocarbon oils for the purposes of the invention. Other compatible hydrocarbon oils include paraffins, lipids, waxes, glycerides, fatty acids, natural and synthetic hydrocarbon oils and derivatives thereof. Preferred natural hydrocarbon oils may be selected from the group consisting of canola oil, soybean oil, olive oil, corn oil, castor oil, safflower oil and sunflower oil.

In preferred embodiments, the fluorophilic dispersing agent is selected from the group consisting of semifluorinated alkanes or alkenes and perfluoroalkylated surfactants. In particularly preferred embodiments, the dispersing agent is selected from the group consisting of diblock compounds having the general formula $C_nF_{2n+1}C_mH_{2m+1}$ (saturated) or the general formula $C_nF_{2n+1}C_mH_{2m-1}$ (unsaturated), wherein n is an integer from 2–12 and m is an integer from 2–16. In other preferred embodiments, the fluorophilic dispersing agent is selected from fluorinated surfactants such as those described in "Fluorinated Surfactants Intended for Biomedical Uses," J. Greiner, J. G. Riess and P. Vierling in *Organofluorine Compounds in Medicinal Chemistry and Biomedical Applications,* R. Filler, T. Kobayashi and Y. Yagupolski (eds.), Elsevier, 339–380 (1993). Moreover, as indicated above, these dispersions may comprise a bioactive agent, preferably a lipophilic bioactive agent, that associates with, or forms, the disperse hydrocarbon oil phase.

Fluorochemicals compatible with the present invention are generally selected for beneficial physical characteristics such as low toxicity, low surface tension, high spreading coefficient and the ability to transport gases. More specifically, compatible fluorochemicals include, but are not limited to, perfluorochemicals, partially fluorinated compounds, substituted and unsubstituted compounds, and various fluorochemical derivatives. In particularly preferred embodiments the selected fluorochemicals are halogenated.

As previously alluded to, the HO/FC preparations of the present invention may be combined with a polar liquid and at least one emulsifying agent to provide a hydrocarbon oil-in-fluorochemical-in-polar liquid (HO/FC/W) multiple emulsion. The multiple HO/FC/W emulsions may be prepared by adding the HO/FC emulsion, under gentle stirring, to a water phase containing at least one emulsifying agent (e.g., phospholipids) to give an emulsion preparation. In other embodiments, the multiple emulsions of the present invention may be prepared by combining the components, including at least one hydrocarbon oil, at least one fluorochemical, a fluorophilic dispersing agent, a polar liquid and an emulsifying agent prior to emulsification. In either case, those skilled in the art will appreciate that the desired multiple emulsion may form spontaneously or can be formed using ultrasound, microfluidization, high pressure homogenization or any other appropriate method. The external water phase of the resulting multiple emulsion can be demonstrated by the ability to dilute the HO/FC/W emulsion with water (but not with a fluorochemical) without forming a new phase boundary.

Accordingly, one aspect of the present invention is a hydrocarbon oil-in-fluorochemical-in-polar liquid multiple emulsion comprising:
a disperse phase comprising at least one hydrocarbon oil, at least one fluorochemical and an effective dispersing amount of at least one fluorophilic dispersing agent; and
a continuous phase comprising at least one polar liquid having at least one emulsifying agent dispersed therein.

In preferred embodiments the incorporated emulsifying agent is more hydrophilic than the incorporated fluorophilic dispersing agent. Of course those skilled in the art will appreciate that any emulsifying agent which provides the desired multiple emulsion may be incorporated in the preparations of the present invention. Preferably the emulsifying agent is selected from the group consisting of phospholipids, poloxamers (such as pluronics), poloxamines (such as tetronics) and sorbitan esters. In particularly preferred embodiments the emulsifying agent is a phospholipid or combination of phospholipids such as egg yolk phospholipid (EYP). Moreover, in selected embodiments the polar liquid will be water or an aqueous based solution.

The multiple emulsions of the present invention may preferably comprise from about 0.01% to about 50% (v/v) of at least one hydrocarbon oil, 1% to about 95% (v/v) of at least one fluorochemical, 0.0005% to about 70% (v/v) of at least one fluorophilic dispersing agent, 5% to about 99% (v/v) of at least one polar liquid and 0.01% to about 20% (w/v) of at least one emulsifying agent. As with the HO/FC dispersions discussed above, these emulsions may comprise a bioactive agent which, in preferred embodiments, will be a lipophilic bioactive agent that associates with the hydrocarbon oil/fluorochemical disperse phase. Conversely, the hydrocarbon oil itself may have inherent bioactive characteristics. Other additives, including those that contribute to emulsion stability, drug solubility and control of drug delivery profiles, may also be incorporated in the HO/FC/W emulsions of the present invention.

Another aspect of the present invention comprises methods for forming HO/FC preparations including hydrocarbon oil/fluorochemical (HO/FC) dispersions and hydrocarbon oil-in-fluorochemical-in-polar liquid (HO/FC/W) multiple emulsions. It will be appreciated by those skilled in art that a variety of methods may be used to effectively form the preparations of the present invention and that any process providing the desired dispersion or emulsion is within the scope of this disclosure. In particular, the order in which the components of the preparation, including any bioactive agent, are combined is not necessarily critical and may be altered for ease of production or other reasons. For example, in one preferred embodiment all the components of the dispersion or the multiple emulsion are combined prior to formation of the desired preparation. In other preferred embodiments an HO/FC dispersion is formed (optionally comprising a bioactive agent) and, after an indeterminate period, this dispersion may be combined with a continuous phase comprising a polar liquid and an emulsifying agent to provide a multiple emulsion. Compatible components and preferred concentrations are as detailed above. In select embodiments a bioactive agent, and in particular a lipophilic agent, is associated with the HO/FC disperse phase while in others a bioactive agent may be combined with the continuous polar liquid phase. Co-solvents may be employed in either case to facilitate association of the bioactive agent with the selected phase.

In yet another aspect, the present invention provides methods for delivering a bioactive agent to a patient using the disclosed HO/FC preparations including HO/FC dispersions and HO/FC/W multiple emulsions. As used herein, the term bioactive agent is defined to mean any pharmaceutical compound or composition, including diagnostic and therapeutic agents as well as physiologically acceptable gases such as oxygen or nitric oxide, which may be administered to an animal to treat a disorder. In general the method comprises:
providing a bioactive preparation comprising a hydrocarbon oil/fluorochemical preparation and at least one bioactive agent; and
administering said bioactive preparation to a patient.

As discussed above, the bioactive preparation may comprise a bioactive agent in the form of a hydrocarbon oil solubilized by the incorporated dispersing agent or it may comprise a bioactive agent associated with a solubilized hydrocarbon oil. In accordance with the teachings herein the bioactive preparations of the present invention may be administered to a patient using a route of administration selected from the group consisting of topical, subcutaneous, pulmonary, intravenous, sinovial, intramerial, intramuscular, intraperitoneal, nasal, vaginal, rectal, aural, oral and ocular routes. Due to the physical characteristics of the HO/FC bioactive dispersions, pulmonary administration and administration to the gastrointestinal tract of these preparations is particularly preferred. Conversely, bioactive preparations comprising HO/FC/W multiple emulsions are preferred for intravenous administration.

Pharmaceutically effective amounts of both lipophilic bioactive agents and those which are soluble in water may be advantageously delivered using the preparations of the present invention. Preferably, water soluble bioactive agents are delivered using multiple emulsions having a liquid polar phase, typically in combination with a lipophilic agent associated with the disperse phase. Lipophilic bioactive agents, associated with the HO/FC component of the bioactive preparation, preferably in the form of a solubilized hydrocarbon oil, may be effectively delivered using either the HO/FC dispersions or the HO/FC/W multiple emulsions. In each of the aforementioned embodiments, bioactive agents compatible with the present invention include, but are not limited to, respiratory agents, antibiotics, antivirals, mydriatics, antiglaucomas, anti-inflammatories, antihistaminics, antineoplastics, anesthetics, ophthalmic agents, enzymes, cardiovascular agents, active principles, nucleic acids, genetic material, viral vectors, immunoactive agents, imaging agents, immunosuppressive agents, peptides, proteins, physiological gases and gastrointestinal agents. Pharmaceutically effective amounts of the selected bioactive agents may be determined using techniques well known in the art. Additional solubilizing or dispersing agents such as, for example, dimethylsulfoxide, polyethylene glycol, sorbitan esters poloxamers such as pluronics or poloxamines can be used to facilitate the incorporation of the selected bioactive agents or agents into one or the other phase of the preparation.

Other objects, features and advantages of the present invention will be apparent to those skilled in the art from a consideration of the following detailed description of preferred exemplary embodiments thereof taken in conjunction with the associated Figures which will first be described briefly.

BRIEF DESCRIPTION OF THE FIGURES

FIG. 4 is a graphical representation illustrating particle size distribution of F6H14 micelles containing methyl salicylate, a bioactive agent, in F-octanes.

DETAILED DESCRIPTION OF THE PRESENT INVENTION

Figure 1:
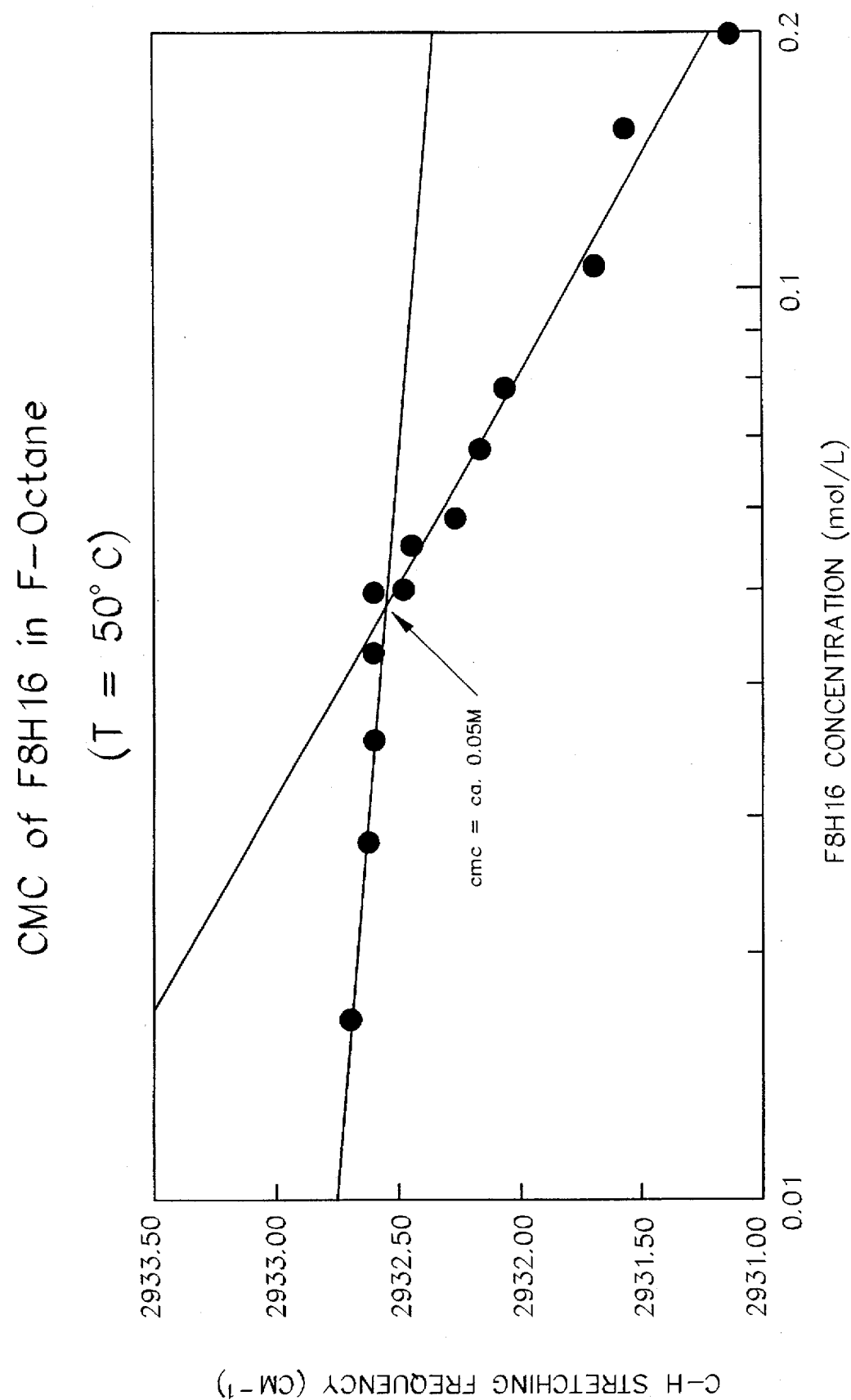
FIG. 1 is a graphical representation illustrating the change in —$CH_2$ stretching frequency vs FSH16 concentration wherein the inflection point evidences the formation of FSH16 micelles.

In a broad aspect the present invention provides hydrocarbon oil/fluorochemical (HO/FC) preparations that may be used for controlled administration of bioactive agents. Preferred embodiments of the present invention comprise hydrocarbon oil-in-fluorochemical (HO/FC) dispersions and hydrocarbon oil-in-fluorochemical-in-polar liquid (HO/FC/W) multiple emulsions. The HO/FC dispersions typically comprise a fluorochemical continuous phase into which a hydrocarbon oil is dispersed. In select embodiments the dispersed hydrocarbon oil may comprise a bioactive agent. These dispersions are preferably stabilized through the use of a fluorophilic dispersing agent. Preferably, the HO/FC/W multiple emulsions comprise a disperse phase (or HO/FC phase) comprising hydrocarbon oil particulates, or droplets, at least partially encapsulated in fluorochemical. In such embodiments the fluorochemical encapsulated hydrocarbon oil droplets are dispersed in a continuous polar liquid phase comprising a hydrophilic emulsifying agent. A fluorinated surfactant or a fluorocarbon-hydrocarbon diblock compound and natural phospholipids can be used, for example, as the fluorophilic and as the emulsifying agents, respectively.

HO/FC preparations, both in the form of HO/FC dispersions and HO/FC/W emulsions, have utility as vehicles and controlled release systems for bioactive agents, and lipophilic material in general. With the HO/FC dispersions and HO/FC/W multiple emulsions of the present invention, the diffusion of a lipophilic drug, comprising or associated with the encapsulated hydrocarbon oil droplet may be significantly retarded by the fluorochemical shell. These properties allow for controlled drug release and prolonged delivery profiles, particularly for lipophilic bioactive agents. The fluorochemical barrier can also act to protect the encapsulated substances from body fluids and vice-versa, thus reducing the toxicity of the incorporated substances.

The partially fluorinated or perfluorinated compounds comprising the fluorochemical component of the disclosed preparations, both HO/FC and HO/FC/W, are typically chosen for their low toxicity, gas dissolving capacity, surface tension and spreading coefficient. Particularly preferred fluorochemicals will be capable of delivering therapeutically significant amounts of gases including nitric oxide or oxygen. In general, the highly fluorinated or perfluorinated compounds may be linear, branched or cyclic, saturated or unsaturated fluorinated compounds. Conventional structural derivatives of these fluorochemicals are also contemplated as being within the scope of the present invention as well. In addition, these totally or partially fluorinated compounds may contain one or more hetero-atoms and/or atoms of bromine or chlorine. The term "partially fluorinated" indicates that at least 60% of the hydrogen atoms in the hydrocarbon oil or derivative thereof have been replaced with fluorine atoms. Preferably, these fluorochemicals comprise from 2 to 16 carbon atoms and include, but are not limited to, linear, cyclic or polycyclic perfluoroalkanes, bis(perfluoroalkyl)alkenes, perfluoroethers, perfluoroamines, perfluoroalkyl bromides and perfluoroalkyl chlorides. Exemplary partially fluorinated fluorochemicals that are compatible with the present invention include $CF_3CH_2F$ (FC 134A), $CHF_2CF_2CH_2F$ (FC 245ca) and $CHF_2CHF_2$ (FC134). The aforementioned compounds may be used either alone or in combination.

In a preferred embodiment of the invention the incorporated fluorinated compound comprises perfluorooctyl bromide, $C_8F_{17}Br$ (PFOB or perflubron) or of perfluorooctylethane $C_8F_{17}C_2H_5$ (PFOE). Other preferred fluorochemicals include perfluoroctane $C_8F_{18}$, perfluorodecane, $C_{10}F_{22}$, perfluorodecyl bromide $C_{10}F_{21}Br$ (PFDB), his (perfluorobutyl) ethene (F-44E) or perfluorodecalin (FDC). In addition to the aforementioned compounds, exemplary fluorochemicals which are contemplated for use in the present invention generally include halogenated fluorochemicals (i.e. $C_nF_{2n+1}X$, $XC_nF_{2n}X$, where n=2–10, X=Br, Cl or I) and, in particular, 1bromo-F-butane n-$C_4F_9Br$, 1-bromo-F-hexane (n-$C_6F_{13}BR$, 1-bromo-F-heptane (n-$C_7F_{15}Br$), 1,4-dibromo-F-butane and 1,6-dibromo-F-hexane. Other useful brominated fluorochemicals are disclosed in U.S. Pat. No. 3,975,512 to Long and are incorporated herein by reference. Specific fluorochemicals having chloride substituents, such as perfluorooctyl chloride (n-$C_8F_{17}Cl$), 1,8-dichloro-F-octane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon oil compounds and halogenated fluorochemicals containing other linkage groups, such as esters, thioethers and amines are also suitable for use in forming the compositions of the present invention. For instance, compounds having the general formula, $C_nF_{2n+1}OC_mF_{2m+1}$, or $C_nF_{2n+1}CH=CHC_mF_{2m+1}$, (as for example $C_4F_9CH=CHC_4F_9$ (F-44E), i-$C_3F_9CH=CHC_6F_{13}$ (F-i36E), and $C_6F_{13}CH=CHC_6F_{13}$ (F-66E)) where n and m are the same or different and n and m are integers from about 2 to about 12 are compatible with teachings herein. Useful fluorochemical-hydrocarbon diblock and triblock compounds include those with the general formulas $C_nF_{2n+1}$-$C_mH_{2m+1}$ and $C_nF_{2n+1}C_mH_{2m-1}$, where n=2–12; m=2–16 or $C_pH_{2p+1}$-$C_nF_{2n}$-$C_mH_{2m+1}$, where p=1–12, m=1–12 and n=2–12. Preferred compounds of this type include $C_8F_{17}C_2H_5$, $C_6F_{13}C_{10}H_{21}$, $C_8F_{17}C_8H_{17}$, $C_6F_{13}CH=CHC_6H_{13}$ and $C_8F_{17}CH=CHC_{10}H_{21}$. Substituted ethers or polyethers (i.e. $XC_nF_{2n}OC_mF_{2m}X$, $XCFOC_nF_{2n}OCF_2X$, where n and m=1–4, X=Br, Cl or I) and fluorochemical-hydrocarbon ether diblocks or triblocks (i.e. $C_nF_{2n+1}$-O-$C_mH_{2m+1}$, where n=2–10; m=2–16 or $C_pH_{2p+1}$-O-$C_nF_{2n}$-O-$C_mH_{2m+1}$, where p=2–12, m=1–12 and n=2–12) may also used as well as $C_nF_{2n+1}$O-$C_nF_{2m}$O$C_p$ $H_{2p+1}$, wherein n m and p are from 1–12. Furthermore, depending on the application, perfluoroalkylated ethers or polyethers may be compatible with the HO/FC dispersions.

Polycyclic and cyclic fluorochemicals, such as $C_{10}F_{18}$ (F-decalin or perfluorodecalin) and a mixture of perfluoroperhydrophenanthrene and of perfluoro n-butyldecalin are also within the scope of the invention. Additional useful fluorochemicals include perfluorinated amines, such as F-tripropylamine ("FTPA") and F-tributylamine ("FTBA"). F-4-methyloctahydroquinolizine ("FMOQ"), F-N-methyldecahydroisoquinoline ("FMIQ"), F-N-methyldecahydroquinoline ("FHQ"), F-N-cyclohexylpyrrolidine ("FCHP") and F-2-butyltetrahydrofuran ("FC-75" or "FC-77") may also be incorporated. Other contemplated fluorochemicals having nonfluorine substituents, such as, perfluorooctyl hydride, and similar compounds having different numbers of carbon atoms are also useful. Those skilled in the art will further appreciate that other variously modified fluorochemicals are encompassed within the broad definition of fluorochemical suitable for use in the present invention.

In preferred embodiments, the HO/FC/W multiple emulsions of the invention contain from 1% to 95% (v/v), and more preferably from 30% to 60% (v/v) of fluorochemical. The HO/FC dispersions contain from 25% to 99.9% (v/v), and more preferably from 60% to 98% (v/v) of fluorochemical.

To form and stabilize the desired HO/FC preparations, fluorophilic dispersing agents, preferably comprising fluorochemical-hydrocarbon diblocks or fluorinated surfactants, may be incorporated as previously described. The fluorophilic dispersing agent acts at the interface between the incorporated hydrocarbon oil and fluorochemical to allow incorporation of the initially phase-separated hydrocarbon oil in the fluorochemical. As previously discussed, exemplary fluorophilic dispersing agents comprise fluorinated surfactants and fluorochemical-hydrocarbon diblock molecules. Generally, the selected fluorophilic dispersing agent will comprise from about 0.0005% to about 75% (v/v) and more preferably from about 0.01% to about 5% (v/v) of the multiple emulsion and from about 0.01% to about 99% (v/v) and more preferably from about 0.1% to about 50% (v/v) of an HO/FC dispersion.

In preferred embodiments of the present invention, the fluorophilic dispersing agent comprises diblock molecules which comprise compounds of the following general formula:

$$R_F\text{-}L\text{-}R_H\text{-}Z$$

wherein, $R_F$ is one or more perfluorinated or partially fluorinated groups which may or may not contain branches and/or ring structures or hetero-atoms (ex. $CF_3(CF_2)_m$—, $CF_3CF_2CF(CF_3)(CF_2)_m$—; m=integer);

$R_H$ is one or more hydrocarbon groups which may or may not contain branches and/or ring structures and/or hetero-atoms and/or multiple bonds (ex. —$(CH_2)_n$—, —$C_6H_4$ $(CH_2)_4$—, —$(CH_2)_pO(CH_2)_q$—, —$(CH_2)_2CH=CH$ $(CH_2)_5$—; n, p and q=integer;

L is a variable linkage unit and may contain, but is not limited to one or more of the following: —$CH_2$—, —$CH=CH$—, —O—, —S—, —$PO_4$-, etc.; and Z is H or a group more polar or polarizable than the $R_H$ groups (ex. allyl ethers as in: $CF_3(CF_2)_x$—$(CH_2)_n$—O $(CH_2)_mCH=CH_2$ or an alcohol or a halogen wherein x=1–11 and n or m=1–16).

More specifically, in particularly preferred embodiments diblock compounds utilized as dispersants are of general formula $R_FLR_H$, where $R_F$ is typically one or more fluorinated alkane of 2 to 12 carbon atoms, $R_H$ is one or more linear, branched or cyclic, saturated or unsaturated alkane of 2 to 16 carbon atoms, and L is a linkage unit comprising, for example, a single carbon-carbon bond or an oxygen atom or any other suitable moiety.

In still another preferred embodiment the diblock compound is selected from the group consisting of compounds having the formula $C_nF_{2n+1}C_mH_{2m+1}$ (saturated), compounds having the formula $C_nF_{2n+1}C_mH_{2m-1}$ (unsaturated) and combinations thereof, wherein n is an integer from 2 to 12 and m is an integer from 2 to 16.

Other fluorophilic dispersing agents useful in the present invention include fluorinated surfactants which preferably contain at least four fluorine atoms. These fluorinated surfactants can be of different types. Classes of fluorinated surfactants contemplated for use in the present invention include, for example, amphiphiles containing phosphorus (e.g., (perfluoroalkyl)alkylene mono- or dimorpholinophosphate and fluorinated phospholipids) or alcohols, polyols or polyhydroxylated or aminated derivatives including amine oxides and amino acid derivatives. Such fluorinated surfactants are described, for example, in EP-A-0 255 443, FR-A-2 665 705, FR-A-2 677 360, FR-A- 2 694 559, FR-A- 2 679 150, WO90/15807 U.S. Pat. No. 3,828,085 and EP-A-0311473 and in "Fluorinated Surfactants Intended for Biomedical Uses", J. Greiner, J. G. Riess and P. Viefling in *Organofluorine Compounds in Medicinal Chemistry and Biomedical Applications*, R. Filler, T. Kobayashi and Y. Yagupolski (eds.), Elsevier, 339–380 (1993) each of which is incorporated herein by reference. In a particularly preferred embodiment, the HO/FC dispersions of the invention contain the (perfluoroalkyl)alkylene phosphate of the formula:

$$R_FR_1OP(O)[N(CH_2CH_2)_2O]_2 \text{ or } [R_FR_1O]_2P(O)[N(CH_2CH_2)_2O]$$

wherein $R_F$ is $CF_3(CF_2)_t$ such that t is from 1 to 11 and $R_1$ is a saturated or unsaturated, linear or branched hydrocarbon chain and both $R_F$ and $R_1$ may contain at least one oxygen and/or sulfur atom.

The fluorinated surfactants may also be associated with hydrogenated, non-ionic, anionic, cationic or zwitterionic surfactants. Such hydrogenated surfactants include, for example, phospholipids, copolymers of the polyoxyethylene polyoxyethylenepolyoxypropylene type (e.g., PLURONIC F-68®) and polyoxyethylene sorbitan esters. Further, mixtures of the fluorophilic dispersing agents are also contemplated as being within the scope of the present invention as long as they produce the desired HO/FC preparations.

As previously described, the disclosed fluorochemicals and fluorophilic dispersing agents may be combined with a hydrocarbon oil to provide a hydrocarbon oil-in-fluorochemical (HO/FC) dispersion. Depending on parameters such as formulation, processing and temperature, the dispersions of the present invention may comprise an emulsion, a microemulsion, a micellar solution or any other such colloidal system. For example, the dispersion may comprise a transparent, sometimes bluish microemulsion at room temperature and a whitish macroemulsion below room temperature. Particularly preferred embodiments comprise thermodynamically stable microemulsions. As will be appreciated by those skilled in the art, thermodynamically stable microemulsions are resistant to coarsening (which should increase the shelf-life of any incorporated bioactive agent) and are generally characterized by small (average diameter $\leq 100$ nm), relatively narrow particle size distributions. Moreover, the homogenous distribution of the bioactive hydrocarbon oil or hydrocarbon oil comprising a bioactive agent in such systems will promote reproducible delivery profiles and reliable dosing regimens.

In the HO/FC dispersions of the present invention the hydrocarbon oil component comprises from about 0.01% to about 75% (v/v) of the dispersion and more preferably from about 0.1% to about 30% (v/v). Preferably, the hydrocarbon oil will constitute from about 0.01% to about 50% (v/v) of a HO/FC/W multiple emulsion and more preferably from about 0.5% to about 15% (v/v).

It must be emphasized that any compound or agent which may be solubilized by the disclosed fluorophilic dispersing agents and incorporated into the described HO/FC dispersions or the HO/FC/W multiple emulsions is considered a hydrocarbon oil for the purposes of the present invention. That is, in preferred embodiments the hydrocarbon oil may comprise one or more lipophilic bioactive agents. Specifically, the hydrocarbon oils of the present invention may comprise one or more bioactive agents, one or more non-bioactive agents or a combination of bioactive agents and non-bioactive agents. In particularly preferred embodiments the bioactive preparations of the present invention contain a hydrocarbon oil comprising one or more bioactive agents dispersed in a fluorochemical phase along with at least one fluorophilic dispersing agent. While not limiting the invention in any manner, it is believed the fluorophilic dispersing agent can, in some embodiments, form micelles that solubilize the lipophilic bioactive agent in the continuous fluorochemical phase. It will further be appreciated that such systems may be used to form thermodynamically stable microemulsions having improved bioavailability and prolonged delivery profiles.

Of course, such HO/FC systems may also be combined with a polar liquid at taught herein to form multiple emulsions exhibiting superior delivery characteristics. Specifically, it is believed that some or all of the incorporated lipophilic bioactive agents may be compartmentalized or solubilized as a hydrocarbon oil particulate (alone or along with at least one other hydrocarbon oil) which, in most cases, is then at least partially encapsulated by the fluorochemical component of the HO/FC dispersion. That is, it appears in some embodiments that the fluorochemical component of the discontinuous HO/FC phase largely coats the hydrocarbon oil component (and any lipophilic bioactive agent associated with it) of the dispersion or multiple emulsion. This arrangement appears to retard diffusion of any hydrocarbon oil (whether on not it comprises a bioactive agent) into the continuous polar liquid phase or aqueous physiological environment where it would be subject to degradative forces.

While the molecular configuration of the selected hydrocarbon oil is not critical, particularly preferred hydrocarbon oils will be biocompatible and/or bioactive. Hydrocarbon oils compatible with the present invention may comprise hydrocarbons, and derivatives thereof, having straight or branched chains, be cyclic, aliphatic or aromatic and be substituted or unsubstituted. Further, the selected hydrocarbon oil or hydrocarbon oils may contain a charged substituent. Exemplary biocompatible hydrocarbon oils that may be used include naturally occurring oils such as canola oil, safflower oil, soybean oil, olive oil, corn oil, castor oil, sunflower oil and derivatives thereof. Moreover, naturally occurring compounds such as phospholipids, lipids, glycerides and other fatty acid derivatives may be used to form the desired emulsion. For example, triglycerides and, in particular, medium chain triglycerides may be incorporated in the bioactive formulations of the present invention. Furthermore, the selected hydrocarbon oil may be synthetic or partially synthetic. In addition mixtures of different hydrocarbon oils, both bioactive and non-bioactive, may be used.

The HO/FC dispersions and multiple emulsions of the present invention are capable of delivering any desired bioactive agent that may be incorporated in either the disperse phase, the continuous phase or at the interface between the phases. Lipophilic agents may be combined with the HO/FC dispersion (or disperse phase preparation in the case of multiple emulsions) either prior to or after formation. Conversely, any water soluble bioactive agent may be combined with the continuous phase preparation used to form the selected multiple emulsion. As used herein, the term bioactive agent is defined to mean any pharmaceutical compound or composition, including diagnostic and therapeutic agents as well as physiologically acceptable gases such as oxygen or nitric oxide, which may be administered to an animal to treat a disorder. Preferred bioactive agents include hydrophilic drugs with solubility in water and lipophilic drugs. Most preferably, bioactive agents are lipophilic agents which are associated with the disperse HO/FC phase in the case of multiple emulsions and primarily with the hydrocarbon oil in the case of hydrocarbon oil-in-fluorochemical dispersions.

As discussed, bioactive hydrocarbon oils or bioactive agents associated with hydrocarbon oils incorporated in the preparations of the present invention are preferably lipophilic. In preferred embodiments the selected hydrocarbon oil will be partially or entirely lipid soluble. Similar to the fluorochemicals discussed above, the selection of compatible bioactive agents, is limited only by the ability to incorporate them in the desired HO/FC dispersions or multiple emulsions as disclosed in the present invention. Yet, some indication as to the ability of an individual bioactive agent to be incorporated in the disclosed preparations as a hydrocarbon oil may be derived from the measured value of its lipophilicity. The convention is to measure and report the lipophilicity of a bioactive agent using the log of the octanol/water partition coefficient (Log $P_{o/w}$). In this system increasing lipophilicity corresponds to higher Log $P_{o/w}$ values. Preferably, lipophilic bioactive agents incorporated in the present invention will have a Log $P_{o/w}$ greater than about 0.5. More preferably the lipophilic bioactive agents will have a Log $P_{o/w}$ greater than about 2.0. As those skilled in the art will appreciate, values such as these indicate that a compound has limited solubility in an aqueous environment. The octanol/water partition coefficients of several exemplary lipophilic bioactive agents compatible with the teachings of the present invention, are reproduced below in Table 1.

TABLE 1

Octanol/water partition coefficients (Po/w) of various drugs

| Drug Substance | $P_{o/w}$ | Log $P_{o/w}$ |
|---|---|---|
| $^{14}$C-anthracene[1] | $3.16 \times 10^4$ | 4.5 |
| $^{14}$C-bunolol[1] | $2.51 \times 10^2$ | 2.4 |
| $^{14}$C-cimetidine[1] | 2.51 | 0.4 |
| $^{14}$C-hexamethylene lauramide[1] | $2.00 \times 10^7$ | 7.3 |
| $^{14}$C-padimate-o[1] | $3.98 \times 10^6$ | 6.6 |
| $^{14}$C-progesterone[1] | $7.9 \times 10^3$ | 3.9 |
| $^{14}$C-testosterone[1] | $2.00 \times 10^3$ | 3.3 |
| $^3$H-clonidine[1] | 25.1 | 1.4 |
| $^3$H-diethylstilbesterol[1] | $1.26 \times 10^5$ | 5.1 |
| $^3$H-fluorometholone[1] | $1.26 \times 10^2$ | 2.1 |
| $^3$H-parsol 1789[1] | $5.0 \times 10^6$ | 6.7 |
| valeryl acyclovir[2] | 2.01 | 0.30* |
| hexanoyl acyclovir[2] | 8.58 | 0.93* |
| lidocaine[3] | 2.88 | 0.46 |
| bupivacaine[3] | 28.2 | 1.45 |
| tetracaine[3] | 79.4 | 1.90 |
| halothane[4] | $2.00 \times 10^2$ | 2.30 |
| ampicillin[4] | 11.5 | 1.06 |
| oxazepam[4] | $1.78 \times 10^2$ | 2.25 |
| pentazocin[5] | 150 | 2.18* |
| nitrazepam[5] | 162 | 2.21* |
| haloperidol[5] | 485 | 2.69* |
| biperiden[5] | 678 | 2.83* |
| diazepam[5] | 970 | 2.99* |
| promethazine[5] | $1.27 \times 10^3$ | 3.10* |
| trihexyphenidyl[5] | $1.47 \times 10^3$ | 3.17* |
| chlorpromazine[5] | $1.90 \times 10^3$ | 3.28* |
| clotiazepam[5] | $3.06 \times 10^3$ | 3.49* |
| clomipramine[5] | $3.80 \times 10^3$ | 3.58* |

[1]Tang-Liu, D. D. -S., Richman, J. B. and Liu, S. S., J. Ocul. Pharmac., 1992, 8, 267.
[2]Hughes, P. M. and Mitra, A. K., J Ocul. Pharmac., 1993, 9, 299.
[3]Hageluken, A., Grunbaum, L., Nurnberg, B., Harhammer, R., Schunack, W. and Seifert, R., Biochem. Pharmac., 1994, 47, 1789.
[4]Moriguchi, I., Hirono, S., Liu, Q., Nakagome, I. and Matsuchita, Y., Chem. Pharm. Bull., 1992, 40, 127.
[5]Yokogawa, K., Nakashima, E., Ishizaki, J., Maeda, H., Nagano, T. and Ichimura, F., Pharm. Res. 1990, 7, 691.
*in octanol/pH 7.4 isotonic phosphate buffer at 37°C.

Preferably, the bioactive formulations of the present invention incorporate less than about 50% w/v of a therapeutic or diagnostic agent. Diagnostic agents will typically be incorporated at higher concentrations while hydrocarbon oils comprising a bioactive agent may have the oil concentrations provided above. The precise amount of bioactive agent incorporated in the HO/FC dispersions or multiple emulsions of the present invention is dependent upon the agent of choice, the required dose, and the form of the drug actually used for incorporation. Those skilled in the art will appreciate that such determinations may be made by using well-known pharmacological techniques in combination with the teachings of the present invention.

Preferred bioactive agents comprise hydrophilic and lipophilic respiratory agents, antibiotics, antivitals, mydriatics, antiglaucomas, anti-inflammatories, antihistaminics, antineoplastics, anesthetics, ophthalmic agents, enzymes, cardiovascular agents, active principles, nucleic acids, genetic material, vital vectors, immunoactive agents, imaging agents, immunosuppressive agents, peptides, proteins, physiological gases, gastrointestinal agents and combinations thereof.

Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone acetonide, Flunisolide), xanthines (i.e. theophylline, caffeine), chemotherapentics (i.e. cyclophosphamide, lomustine, methotrexate, cisplatin, carboxy platin, taxane derivatives), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, salbutamol, terbutaline, formoterol) and surfactants. Still other exemplary embodiments include α/β adrenergic blockers (i.e. Normodyne, Trandate), angiotensin converting enzyme inhibitors (i.e. Vasotec), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

Most preferred agents include glucocorticosteroids, taxane derivatives (i.e. Taxol, Taxotere) and the base forms of drags typically administered as the salt derivative (i.e. Gentamicin, Ciprofloxacin). In accordance with the present invention, those skilled in the art will appreciate that various forms of these compounds may be used to modify the therapeutic index of the bioactive agents.

Because the HO/FC dispersions and multiple emulsions of the present invention are uniquely suited for use in a wide variety of physiological applications such as ocular, oral, intravascular, pulmonary, rectal, sinovial, subcutaneous, intramuscular, intraperitoneal, nasal, vaginal, or aural administration of medicaments or diagnostic compounds, a wide variety of bioactive agents may be incorporated therein. Accordingly, the foregoing list of bioactive agents is exemplary only and not intended to be limiting. It will also be appreciated by those skilled in the art that the proper amount of bioactive agent and the timing of the dosages may be determined for the formulations in accordance with already-existing information and without undue experimentation.

In general, a HO/FC dispersion of the present invention may be prepared by combining at least one hydrocarbon oil, an effective dispersing amount of at least one fluorophilic dispersing agent and at least one fluorochemical. Alternatively, the fluorophilic dispersing agent can be added to the phase-separated combination of the hydrocarbon oil (upper phase) and fluorochemical (lower phase). Depending on components and proportions, a transparent, sometimes bluish dispersion with very small colloidal particles, or a coarser, cloudy or white emulsion may be obtained. In the latter case particle size can be reduced by submitting the coarse emulsion to such emulsifying processes as sonication, high pressure homogenization, microfluidization, or any other appropriate emulsifying procedure.

As previously discussed, the prepared HO/FC dispersion may be combined with a continuous liquid polar phase to form the HO/FC/W multiple emulsions of the present invention. Typically, an emulsifying agent or surfactant (compared to the fluorophilic dispersing agent incorporated in the HO/FC dispersion) is combined with the liquid polar phase and HO/FC dispersion to stabilize the resulting multiple emulsion. That is, the emulsifying agent acts at the interface between the liquid polar continuous phase and the emulsified HO/FC disperse phase thereby lowering interfacial tension and providing an interfacial fill resulting in a significant reduction in emulsion coarsening and sharply increasing shelf-life.

Preferably, the emulsifying agent may be selected from natural amphipathic compounds such as phospholipids, particularly phosphatidylcholines, phosphatidylethanolamines and phosphatidic acids, wherein the combined hydrophobic and hydrophilic properties enable the molecule to interface with both the polar liquid phase and fluorochemical system thereby stabilizing the emulsion droplets. It will further be appreciated that there are various species of each class of phospholipids, such as the phosphatidylcholines, comprising different pairings of saturated and unsaturated fatty acids in the glycerol structures. Each of these varied species or combinations thereof that provide the desired stabilization are contemplated for use in the present invention. As phosphatidylcholines (lecithin) confer the desired emulsive properties and are readily available from natural sources such as egg yolk or easily produced synthetically (Avanti Polar Lipids, Pelham, Ala.) their use is particularly preferred. Such phospholipids can be supplemented by fluorocarbon-hydrocarbon compounds of the $R_FLR_HZ$ type described above as these are known to stabilize fluorocarbon-in-water emulsions. Other emulsifying agents suitable for use in this invention include, but are not limited to fluorinated and non-fluorinated glyceroglycolipids, salts of fatty acids, ether linked lipids and diacylphosphates.

Generally, the emulsifying agent comprises from about 0.01% to about 20% (w/v) of the multiple emulsion and, more preferably, from about 0.1% to about 10% (w/v). Those skilled in the art will appreciate that the amount of hydrophilic emulsifying agent incorporated will depend, in part, on the concentration of the HO/FC phase to be emulsified, as well as on the desired final particle size.

The multiple emulsions of the present invention comprise a continuous polar liquid phase in which the HO/FC dispersion forms the HO/FC disperse phase. Typically, this HO/FC phase will comprise from approximately 0.05% to approximately 95% (v/v) and more preferably from about 30% to about 70% (v/v) of the multiple emulsions. In preferred embodiments the continuous phase will be aqueous or aqueous based. However, other polar liquids such as, for example, alcohols, alkyl sulfoxides and combinations thereof may be compatible with the present invention. In particular short chain alcohols (i.e. carbon chain length≦4 carbons) and alkyl sulfoxides such as dimethylsulfoxide may be suitable for use with or without the addition of water.

Further, the polar liquid phase of the multiple emulsion may have additives dissolved therein which provide the emulsions with desirable properties. For example, an osmotic agent may be added to bring the multiple emulsion to physiological isotonicity. In preferred embodiments the osmotic agent may be sodium chloride or it may be a polyhydroxyl compound such as glycerol or a sugar. Other components which may be added to the HO/FC preparations include, but are not limited to, co-solvents co-surfactants, co-dispersants, mineral salts, buffers, stabilizers, oncotic agents, osmotic agents, nutritive agents and combinations thereof.

The HO/FC dispersions and multiple emulsions of the present invention may be formed using a variety of different processes. It should be emphasized that the order the components are combined is not critical as long as the desired HO/FC preparation is produced. Preferably, the desired multiple emulsions are prepared by forming the hydrocarbon oil/fluorochemical (HO/FC) dispersion as previously described and combining it with the polar liquid continuous phase. In one preferred embodiment the fluorophilic dispersing agent is combined with the selected fluorochemical to form a fluorochemical dispersion preparation. The desired amount of hydrocarbon oil is then combined with the preparation along with sufficient energy, if needed, to form the stabilized HO/FC dispersion. In another embodiment the fluorophilic dispersing agent is added to the phase separated mixture of hydrocarbon oil and fluorochemical. In any case, the resulting HO/FC dispersion may then be combined with a continuous phase preparation comprising at least one polar liquid having a hydrophilic emulsifying agent dispersed therein to provide a multiple emulsion preparation. Conversely, the components of the multiple emulsion may be combined without any preformation of the HO/FC dispersion to form the multiple emulsion preparation. Typically, the multiple emulsion preparation is emulsified to produce the HO/FC/W multiple emulsions of the present invention. Preferably, these multiple emulsions comprise an emulsified disperse phase (HO/FC phase) and a continuous phase comprising at least one polar liquid.

As will be appreciated by those skilled in the art, emulsification may require the input of energy to convert an immiscible two phase system into a substantially homogeneous suspension of discontinuous small droplets. In the present invention, either the HO/FC phase formation or the multiple emulsion formation, may be carried out using conventional techniques such as mechanical stirring, vibration, microfluidization, sonication or homogenization under pressure. In addition, dispersion of the hydrocarbon oil in the fluorochemical may, depending on the components and proportions, occur spontaneously upon addition of the dispersing agent.

The disperse phase of the HO/FC dispersions or the emulsified disperse phase of the disclosed multiple emulsions preferably comprises relatively small particulates having an average diameter on the order of nanometers to tens of microns. As used herein, the terms "particles" or "particulates" refers to the emulsion particulates of the discontinuous phase. In the present invention, such small, evenly distributed particles greatly increase the bioavailability of any incorporated bioactive agents (particularly lipophilic agents) at the physiological target site due to their relatively large surface area and effective encapsulation of the therapeutic or diagnostic compound. Moreover, by altering the component concentration, preparation conditions or amount of energy imparted during emulsification, the size of the incorporated HO/FC particulates may be controlled. Those skilled in the art will appreciate that the ability to control the incorporated particle size may be used to attenuate and extend drug delivery profiles to optimize dosing regimes. Preferably, the average particle diameter may be on the order of 1 μm or less and more preferably on the order of 10 nm to 0.5 μm.

The HO/FC preparations of the present invention can be administered via several different routes, depending upon the indication to be treated. For example, intranasal or intrapulmonary administration, aerosolization or nebulization is contemplated for the treatment of respiratory or systemic disorders. This is particularly true of the HO/FC dispersions. An example would include the treatment of lung cancer or other systemic cancers with taxane derivatives by administration of more efficacious forms of existing drugs. Due to its low aqueous solubility paclitaxel (i.e. Taxol) is formulated in a mixture of polyoxyethylated castor oil and ethanol (Bristol-Myers Squibb) which is intended for intravenous administration. In addition to manifestations of hypersensitivity associated with the delivery vehicle itself (i.e. bronchospasm and hypotension) other systemic toxicities associated with paclitaxel such as, cardiac toxicity and neurotoxicity limit the potential usefulness of this drug. The intravenous administration of paclitaxel in the form of a multiple emulsion, or pulmonary administration in the form of a HO/FC dispersion could significantly improve the safety profile of the drug by eliminating the use of biologically active delivery vehicles and by reducing the concentration of the drug in circulation required for efficacy. Intraperitoneal, subcutaneous and ocular administration of the emulsions are also contemplated as well as administration in any other body cavity. The multiple emulsions of the invention may also be used to deliver therapeutic and diagnostic agents to the gastrointestinal tract by, for example, the oral route of administration. A contemplated example would be the delivery of antibiotics to the lining of the gastrointestinal tract in the treatment of *Heliobacter priori* infections. *H. priori* has been implicated in the cause of gastric ulcers and stomach cancer. Antibiotics effective in the treatment of *H. priori* infections could be administered in the form of a dispersion or a multiple emulsion.

It will be appreciated by those skilled in the art that the emulsions of the present invention may be sterilized, for example, by heat, irradiation, ultrafiltration or combinations of any of these or equivalent techniques.

The high bioavailability bioactive preparations of the present invention may advantageously be supplied to the physician in a sterile prepackaged form. More particularly, the formulations may be supplied as stable, preformed multiple emulsions or HO/FC dispersions, ready for administration or as separate, ready to mix components. Typically, when supplied as components, the HO/FC dispersion incorporating a bioactive agent will be packaged separately. This bioactive dispersion could then be mixed, typically by the physician or in a hospital lab, with a sterile polar liquid phase to form the multiple emulsion of the present invention. In such cases, the polar liquid phase could be supplied either by the manufacturer or the final user.

The following nonlimiting examples of various formulations of the present invention illustrate exemplary methods for the their formation and resultant characteristics. For ease of explanation the following definitions shall be used in each of the following examples.

| | |
|---|---|
| 1-(F-hexyl)butane | F6H4 |
| 1-(F-hexyl)decane | F6H10 |
| 1-(F-octyl)hexadecane | F8H16 |
| 1-(F-octyl)hexadecane | F4H8 |
| FmHn | $C_nF_{2n+1}C_mH_{2m+1}$ |
| FnHmE | $C_nF_{2n+1}CH=CHC_mH_{2m+1}$ |

EXAMPLE 1
Micelle formation of F8H16 in perfluorooctanes

A series of solutions of $CF_3(CF_2)_7(CH_2)_{15}CH_3$ (F8H16; 0.02 mol/L to 0.2 mol/L) were prepared in F-octanes (purity≧98%) and the frequency of the carbon to hydrogen (—C—H) stretching mode (T=50° C.) measured using FTIR (Fourier Transform Infrared Spectroscopy). The formation of F8H16 micelles in a fluorocarbon continuous phase results in the transfer of the F8H16 hydrocarbon groups from a fluorocarbon rich environment in the molecular solution to a hydrocarbon rich environment at the interior of the micelles. The occurrence of this phase change can be measured as a change in the FTIR stretching frequency for the carbon-hydrogen bonds in the —$CH_2$ groups of the FmHn molecules. FIG. 1 shows the change in frequency of the C–H stretching mode vs F8H16 concentration. The inflection point in the curve confirmed the existence of F8H16 micelles and was used to define the critical micelle concentration at about 0.05 mol/L.

EXAMPLE 2
Micelle formation of F6H14 in perfluorooctanes

Figure 2:
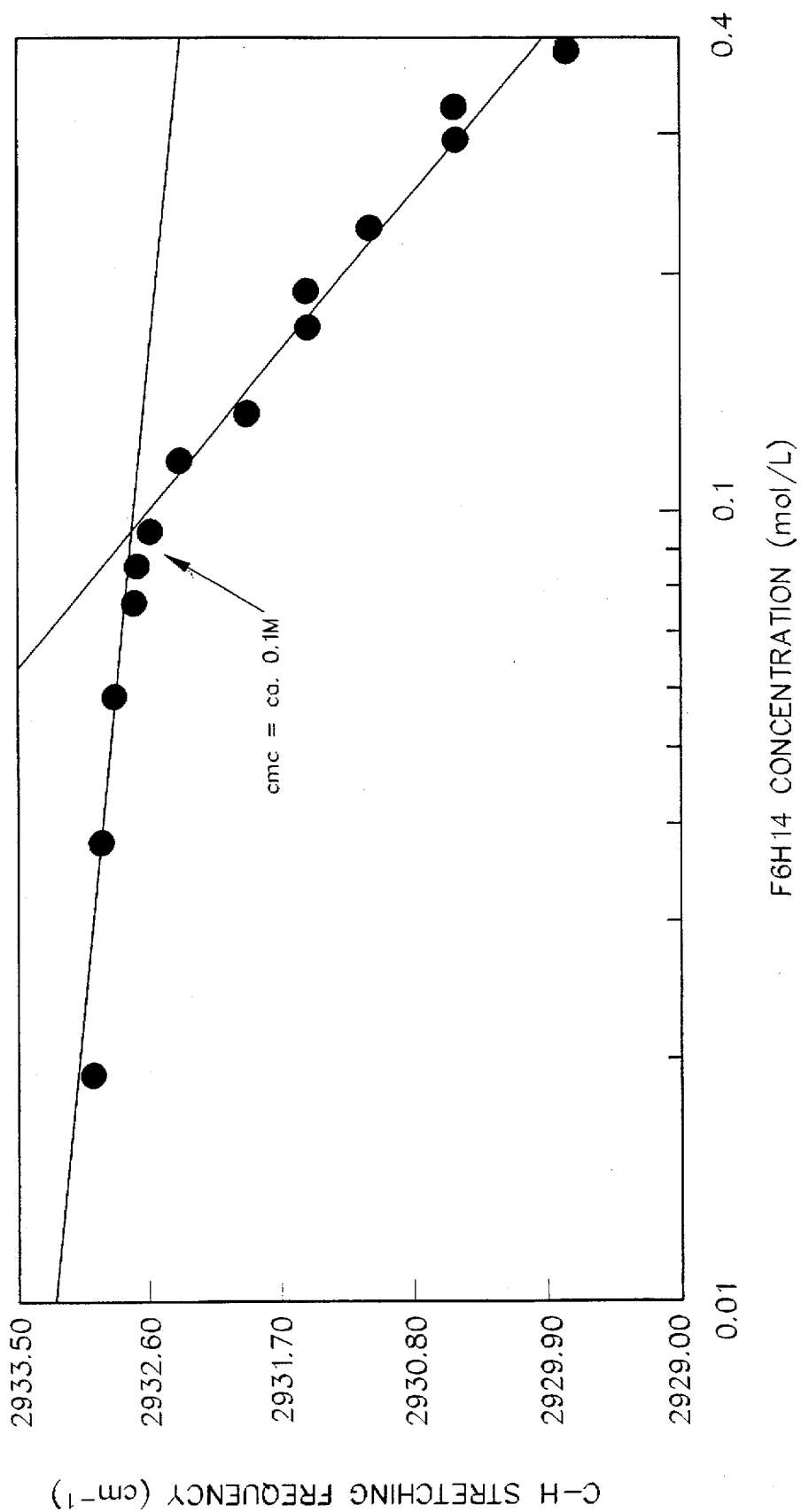
FIG. 2 is a graphical representation showing the change in —$CH_2$ stretching frequency vs F6H14 concentration wherein the inflection point evidences the formation of F6H14 micelles.

A series of solutions of $CF_3(CF_2)_5(CH_2)_{13}CH_3$ (F6H14; 0.02 mol/L to 0.2 mol/L) were prepared in F-octanes (purity≧98%) and the frequency of the carbon to hydrogen (—C—H) stretching mode (T=25° C.) measured using FTIR. The formation of F6H14 micelles was measured as a change in the FTIR stretching frequency for the carbon-hydrogen bonds in the —$CH_2$ groups of the FmHn molecules. FIG. 2 shows the change in frequency of the —C—H stretching mode vs F6H14 concentration. The inflection point in the curve confirmed the existence of F6H14 micelles and was used to define the critical micelle concentration at about 0.1 mol/L.

Figure 3:
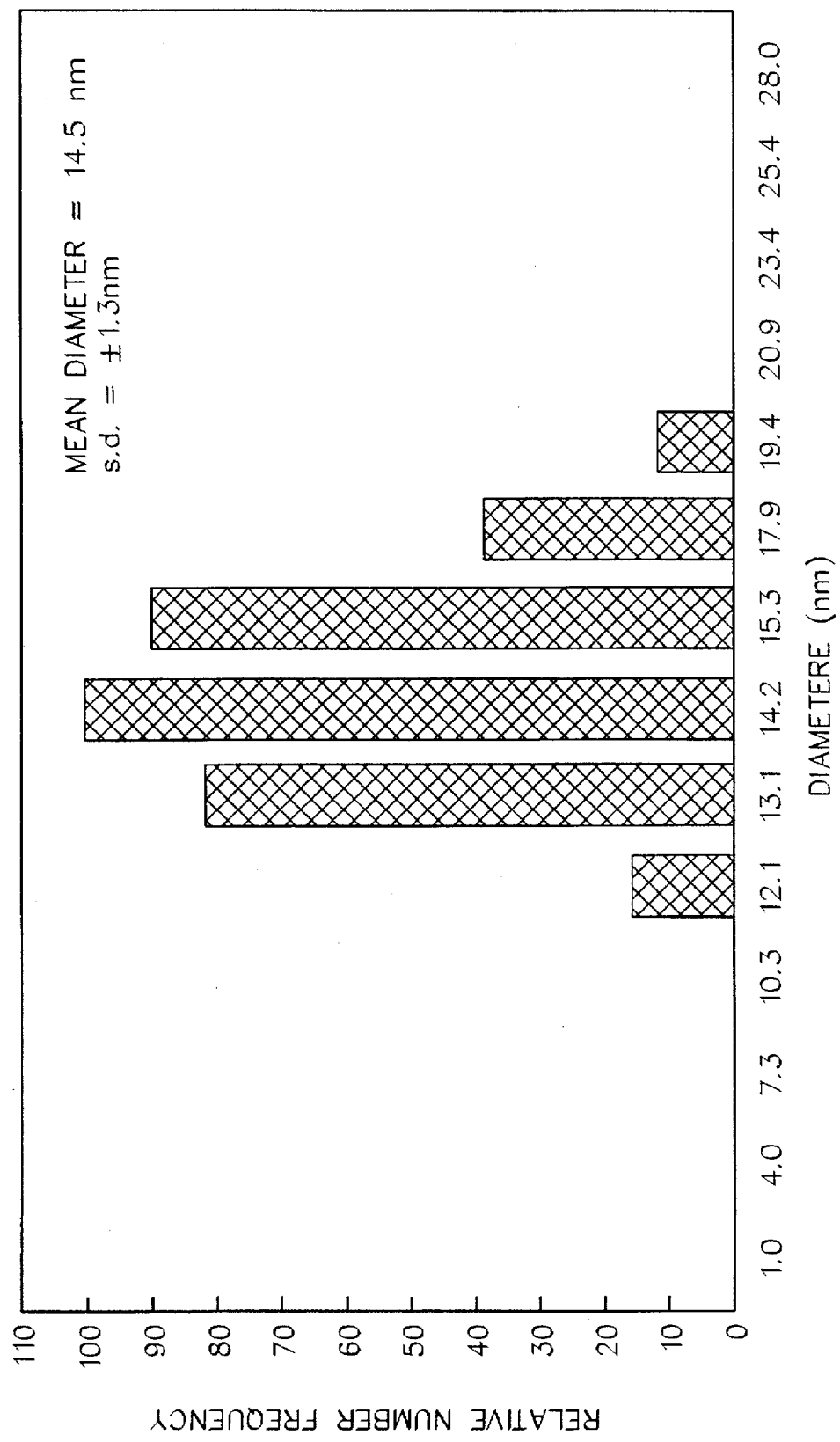
FIG. 3 is a graphical representation illustrating particle size distribution of F8H16 micelles containing n-hexane in F-octanes.

EXAMPLE 3
F8H16 (7.82%, w/v) solubilization of n-hexane (36.5%, v/v) in F-Octanes An aliquot of F-Octanes (8.82 g) was titrated with n-hexane until phase separation occurred (1.70 mL). This was indicated by the formation of a cloudy white mixture which upon siring quickly separated into two clear, colorless phases separated by a distinct interface. F8H16 (0.68 g) was then added to the mixture and the solution mixed to obtain a clear, colorless single liquid phase. The titration with hexane was continued until the solution took on a bluish tint characteristic of microemulsions containing very small droplets (diameter≦100 nm). The system was allowed to equilibrate at 20° C. No indication of phase separation was observed over a 10 day period and the formation of this phase was reversible. The particle size was measured by photon correlation spectroscopy (PCS; Nicomp Model 270 Submicron Particle Sizer) and the number weighted mean diameter determined to be 14.5 nm and relatively monodisperse (standard deviation=±2.7 nm). The fluorocarbon continuous nature of this system was confirmed by the fact that the solution could be diluted with F-octanes without phase separation. When an excess of hydrocarbon (ca 50%, v/v) was added the solution separated into two roughly equivolume clear, colorless liquids with a distinct interface between them. These characteristics were consistent with the formation of F8H16 micelles into which the hydrocarbon oil had been solubilized. The PCS particle size distribution is shown in FIG. 3.

EXAMPLE 4
F6H14 (17.3%, w/v) solubilization of methyl salicylate (2.2%, v/v) in F-Octanes An aliquot of F-Octanes (8.82 g) was titrated with methyl salicylate (a bioactive agent) until phase separation occurred (10–20 µL). F6H14 (1.04 g) was then added to the mixture and the solution mixed to obtain a clear, colorless single liquid phase. The titration with methyl salicylate was continued until the solution took on a bluish tint characteristic of microemulsions containing very small droplets (diameter≦100 nm). The system was allowed to equilibrate at 20° C. and the particle size measured by photon correlation spectroscopy (PCS; Nicomp Model 270 Submicron Particle Sizer). The number weighted mean diameter was measured to be 9.0 nm (standard deviation=±0.8 nm). These characteristics were consistent with the solubilization of methyl salicylate by F6H14 micelles. The PCS particle size distribution is shown in FIG. 4.

EXAMPLE 5
Dispersion comprising heptadecane (9.6% v/v), (F-octyl)butane (3.85% v/v), perfluorooctyl bromide (PFOB) (86.5% v/v)

(F-octyl)butane (0.1 mL) was solubilized in perfluorooctyl bromide (22.5 mL). Heptadecane (2.5 mL) was added to the fluorochemical phase to give a 89.6 v/v hydrocarbon oil/fluorochemical (HO/FC) formulation. Emulsification was achieved by using an ULTRA-TURRAX mixer. The resulting HO/FC emulsion was fluid and slightly gray. The continuous fluorochemical phase was evidenced by the easy dilution of the emulsion in the fluorochemical (perfluorooctyl bromide) and not in the hydrocarbon oil (heptadecane).

EXAMPLE 6
Multiple emulsion comprising heptadecane (4.95% v/v), perfluorooctyl bromide (44.8% v/v), water (50% v/v), (F-octyl)butane (0.2% v/v), and egg yolk phospholipids (1% v/v)

10 mL of the HO/FC emulsion formed in Example 5 was added slowly into a coarse dispersion of phospholipids (0.2 g) in water (10 mL), under gentle stirring. A white emulsion with a continuous water phase, as assessed by easy dilution in water but not in the hydrocarbon oil nor in the fluorochemical, was obtained. The average diameter of the hydrocarbon oil/fluorochemical particles, visible by optical microscopy, was approximately 10 μm. No change in the appearance was observed after 6 monks at room temperature.

EXAMPLE 7
Dispersion comprising perfluorooctyl bromide (PFOB) (90% v/v) [2-(F- octyl)undecyl]dimorpholinophosphate (1% w/v) and heptadecane (10% v/v)

[2-(F-octyl)undecyl]dimorpholinophosphate $C_8F_{17}(CH_2)_{11}OP(O)[N(CH_2CH_2)_2O]_2$ (0.25 g, 1% w/v) was solubilized in perfluorooctyl bromide (22.5 mL) by gentle agitation. Heptadecane (2.5 mL) was added to the fluorochemical phase to give a 90% v/v hydrocarbon oil/fluorochemical (HO/FC) preparation. Emulsification was achieved by using an ULTRA-TURRAX mixer. The resulting HO/FC emulsion had a continuous fluorochemical phase as assessed by dilution of the emulsion in the fluorochemical (perfluorooctyl bromide) but not in the hydrocarbon oil (heptadecane). Appearance of the HO/FC emulsion was whitish and fluid.

EXAMPLE 8
Multiple emulsion containing heptadecane (5% v/v), perfluorooctyl bromide (45% v/v), water (50% v/v), [2-(F-octyl)undecyl]dimorpholinophosphate (1% v/v) and egg yolk phospholipids (1% v/v)

10 mL of the HO/FC emulsion formed in Example 7 was added slowly into a coarse dispersion of phospholipids (0.2 g) in water (10 mL), under gentle stirring. A white emulsion with a continuous water phase, as assessed by easy dilution in water but not in the hydrocarbon oil nor in the fluorochemical, was obtained. No change in the appearance was observed after 6 months at room temperature.

EXAMPLE 9
Dispersion containing perfluorooctyl bromide (PFOB) (95.76%), hexadecane (3.93%) and 1-(F-hexyl)butane (F6H4, 0.305%) [HO/FC=3.87%; F6H4/HC=9.41%]

F6H4 (0.075 g) was solubilized in PFOB (23.52 g). Hexadecane (0.966 g) was added to the fluorocarbon phase. pre-emulsification and emulsification were achieved using an ULTRA-TURRAX mixer and an EMULSIFLEX, model B3 (6000 psi, 3–5 passes) respectively. The resulting HO/FC dispersion was cloudy at 20° C. and transparent at 25° C.

EXAMPLE 10
Dispersion containing PFOB (96.02%), hexadecane (3.65%) and 1-(F-hexyl)decane (F6H10, 0.332%) [HO/FC =3.80%; F6H10/HC=9.09%]

The experimental procedure described in example 9 was applied to the following ingredients and quantities: PFOB (4.34 g), F6H10 (0.015 g), hexadecane (0.165 g). The resulting HO/FC dispersion was transparent at 20° C.

EXAMPLE 11
Dispersion containing bis(F-butyl)ethene (F-44E, 96.32%), dodecane (3.56%) and F6H10 (0.12%) [HO/FC=3.70%; F6H10/FC=3.37%]

The experimental procedure described in example 9 was applied to the following ingredients and quantities; F-44E (9.63 g), dodecane (0.356 g), F6H10 (0.012 g) The resulting HO/FC dispersion was cloudy at 25° C.

EXAMPLE 12
Dispersion containing perfluoroperhydrophenantrene (FPP, 96.16%), dodecane (3.65%) and F6H10 (0.183%) [HO/FC= 3.81%; F6H10/FC=5.01%]

The experimental procedure described in example 9 was applied to the following ingredients and quantities: FPP (9.64 g), dodecane (0.367 g), F6H10 (0.0184 g). The resulting HO/FC dispersion was cloudy at 25° C.

EXAMPLE 13
Dispersion containing PFOB (96.02%), dodecane (3.64%) and 1-(F-hexyl)decane (F6H10, 0.331%) [HO/FC=3.79%; F6H10/FC=9.09%]

A mixture of PFOB (4.35 g) and dodecane (0.165 g) was prepared; it was biphasic. The diblock compound F6H10 (0.015 g) was then added. This led, upon gentle stirring, to a homogenous, transparent phase at 20° C.

EXAMPLES 14–20
This procedure described in example 13, when applied to the following ingredients and proportions led to transparent, homogenous preparation at 25° C.

| Ex. | Fluorochemical | % (v/v) | Hydrocarbon oil | % (v/v) | Diblock % (v/v) FnHm/ FnHmE | HO/FCC (%) | FnHm/HO (%) |
|---|---|---|---|---|---|---|---|
| 14) | PFOB | 95.88 | dodecane | 3.79 | F6H4 0.331 | 3.95 | 8.74 |
| 15) | PFOB | 96.40 | dodecane | 3.47 | F6H10 0.120 | 3.61 | 3.45 |
| 16) | PFOB | 96.41 | dodecane | 3.55 | F6H10 0.033 | 3.69 | 0.92 |
| 17) | PFOB | 96.36 | dodecane | 3.52 | F6H8E 0.120 | 3.65 | 3.41 |
| 18) | PFOE | 96.32 | dodecane | 3.56 | F6H10 0.118 | 3.70 | 3.31 |
| 19) | PFOE | 96.49 | dodecane | 3.44 | F6H10 0.062 | 3.57 | 1.80 |
| 20) | FDC | 96.50 | decane | 3.32 | F4H8E 0.175 | 3.44 | 5.26 |

PFOB = perfluorooctyl bromide; PFOE = perfluorooctylethane; FDC = perfluorodecalin; FnHm = $C_nF_{2n+1}C_mH_{2m+1}$, FnHmE = $C_nF_{2n+1}CH=CHC_mH_{2m+1}$

EXAMPLE 21
Dispersion containing PFOB (88.98%), dodecane (9.98%) and F6H10 (1.03%) [HO/FC=11.22%; F6H10/HC=10.34%]

F6H10 (0.0517 g) was added to a biphasic mixture of PFOB (4.455 g) and dodecane (0.50 g). A coarse dispersion was obtained using an ULTRA-TURRAX mixer. Further emulsification using an EMULSIFLEX homogenizer led to a cloudy emulsion. After 3 days at room temperature a transparent homogeneous phase was obtained.

EXAMPLE 22
Dispersion containing PFOB (85.54%), dodecane (11.65%) and F6H10 (2.93%) [HO/FC=13.64%; F6H10/HC=25%]

The experimental procedure described in example 21 was applied using the following quantities: F6H10 (0.15 g), PFOB (4.40 g), dodecane (0.60 g), leading to a cloudy preparation. After 3 days at room temperature, a transparent homogeneous phase was obtained.

EXAMPLE 23
Dispersion containing PFOB (36.3%), dodecane (35.6%), F6H4 (28.05%), [HO/FC=98.2%; F6H4/HC=78.7%]

A mixture of PFOB (1.10g) and dodecane (1.08 g) was prepared; it was biphasic. The diblock compound F6H4 (0.85 g) was then added. This led, upon gentle stirring, to a bluish fluid homogeneous phase at 25° C. The average size of the microemulsion particulates was 8.6 nm.

EXAMPLE 24
Multiple emulsion containing PFOB (51.62%), hexadecane (2.12%) 1-(F-hexyl)butane (F6H4, 0.165%), egg yolk phospholipids (EYP, 2.19%) and water (43.90%)

The HO/FC preparation (24.56 g) described in example 9 was added slowly into a coarse dispersion of phospholipids (1 g) in water (20 g), under gentle stirring. A white coarse dispersion was obtained. Further emulsification, using an EMULSIFLEX homogenizer (6000 psi, 3–5 passes) led to a white emulsion with an external water phase, as assessed by easy dilution in water but not in hexadecane nor in PFOB. Average particle size was 0.28 µm (photosedimention).

EXAMPLE 25
Multiple emulsion containing PFOB (64.62%), dodecane (2.45%), F6H10 (0.222%), EYP (1.49%) and water (31.2%)

The HO/FC preparation (4.53 g) described in example 13 was added slowly into a coarse dispersion of phospholipids (0.1 g) in water (2.10 g). After emulsification using and EMULSIFLEX homogenizer (6000 psi, 3–5 passes), an hydrocarbon oil-in-fluorocarbon-in-water emulsion with an average particle size of 0.43 µm was obtained.

EXAMPLE 26
Multiple emulsion containing PFOB (77.74%), dodecane (2.88%), F6H10 (0.096%), EYP (2.42%) and water (16.85%)

The HO/FC preparation (10.0 g) described in example 15 was added into a coarse dispersion of phospholipids (0.3 g) in water (2.1 g). After emulsification (EMULSIFLEX 6000 psi, 3–5 passes) a fluorocarbon-in-water emulsion with an average particle size of 0.16 µm was obtained.

EXAMPLE 27
Preparation containing PFOB (96.04%), dodecane (3.60%), F6H10 (0.146%), dimethylsulfoxide (DMSO, 0.158%, and prednisone (0.056%)

Prednisone (0.0057 g) was solubilized in a mixture of dodecane (0.365 g) and DMSO (0.016 g). The latter solution was then added to PFOB (9.724 g), leading to a biphasic mixture. The addition of F6H10 (0.0148 g) then allowed to obtain a transparent homogeneous preparation at 25° C.

EXAMPLE 28
Preparation containing PFOB (96.27%), dodecane (3.34%), F6H10 (0.179%), DMSO (0.167%), and erythromycin stearate (0.046%)

The experimental procedure described in example 27, when applied to the following ingredients and quantities: PFOB (10.72 g), dodecane (0.3715 g), F6H10 (0.020 g), DMSO (0.0186 g), erythromycin stearate (0.0052 g), led to a homogeneous, transparent preparation at 25° C.

EXAMPLE 29
Preparation containing PFOB (95.71%), dodecane (3.63%), F6H10 (0.210%), DMSO (0.394%), and dexamethasone (0.049%%), The experimental procedure described in example 27, when applied to the following ingredients and quantities: PFOB (9.703 g), dodecane (0.368 g), F6H10 (0.0213 g), DMSO (0.040 g), dexamethasone (0.005 g), led to a homogeneous, slightly turbid preparation at 25° C.

EXAMPLE 30
Preparation containing PFOB (96.19%), dodecane (3.56%), F6H10 (0.142%), DMSO (0.048%), and cyclophosphamide (0.051%)

The experimental procedure described in example 27, when applied to the following ingredients and quantities: PFOB (10.052 g), dodecane (0.372 g), F6H10 (0.0148 g), DMSO (0.005 g), cyclophosphamide (0.0053 g), led to a homogeneous, slightly turbid preparation at 25° C.

EXAMPLE 31
Multiple emulsion containing PFOB (58.88%), dodecane (2.21%), F6H10 (0.089%), DMSO (0.097%), and prednisone (0.034%), EYP (2.14%) and water (36.54%)

EYP (0.175 g) was dispersed in water (2.98 g) using an ULTRA-TURRAX mixer. 5.00 g of the preparation described in example 27 was then added to the resulting coarse dispersion of EYP. The mixture was pre-emulsified and emulsified using an ULTRA-TURRAX mixer and an EMULSIFLEX B3 homogenizer (10,000 psi, 5 passes), respectively. A milky hydrocarbon oil-in-fluorocarbon-in-water emulsion was obtained. The average particle size was 0.22 µm (photosedimentation).

EXAMPLE 32
Multiple emulsion containing PFOB (60.35%), dodecane (2.09%), F6H10 (0.112%), DMSO (0.105%), erythromycin stearate (0.029%), EYP (2.19%) and water (35.11%)

The experimental procedure described in example 31, was applied to the following ingredients and quantities: 5.00 g of the preparation described in example 28, water (2.80 g) and EYP (0.175 g). The average particle size of the emulsion was 0.24 µm.

EXAMPLE 33
Multiple emulsion containing PFOB (59.34%), dodecane (2.25%), F6H10 (0.130%), DMSO (0.243%), dexamethasone (0.031%), EYP (2.21%) and water (35.79%)

The experimental procedure described in example 31, was applied to the following ingredients and quantities: 5.04 g of the preparation described in example 29, water (2.91 g) and EYP (0.180 g). The average particle size of the emulsion was 0.20 µm.

EXAMPLE 34
Multiple emulsion containing PFOB (59.55%), dodecane (2.20%), F6It10 (0.088%), DMSO (0.030%), cyclophosphamide (0.032%), EYP (2.17%) and water (35.91%)

The experimental procedure described in example 31 was applied to the following ingredients and quantities: 5.00 g of the preparation described in example 30, water (2.90 g) and EYP (0.175 g). The average particle size of the resulting milky emulsion was 0.20 µm.

EXAMPLE 35

Dispersion containing PFOB (37.08%), dodecane (1.47%), F6H10 (0.128%), Synperonic F108 (2.83%) and DMSO (58.49%)

Synperonic F108 (0.150 g) was solubilized at 30–40°C in DMSO (3.10 g) using an ULTRA-TURRAX mixer. 2.05 g of the preparation described in example 10 was then added to this solution. The mixture was pre-emulsified and emulsified using an ULTRA-TURRAX mixer and an EMULSIFLEX B3 (10000 psi, 5 passes), respectively. A milky triple hydrocarbon-in-fluorocarbon-in-DMSO emulsion was obtained.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A hydrocarbon-based oil-in-fluorochemical preparation comprising:
   a disperse phase comprising at least one hydrocarbon-based oil;
   a continuous phase comprising at least one fluorochemical; and
   an effective dispersing amount of at least one fluorophilic dispersing agent.

2. The preparation of claim 1 wherein said hydrocarbon-based oil comprises at least one bioactive agent.

3. The preparation of claim 2 wherein said at least one bioactive agent is selected from the group consisting of respiratory agents, antibiotics, antivitals, mydriatics, antiglaucomas, anti-inflammatories, antihistaminics, antineoplastics, anesthetics, ophthalmic agents, enzymes, cardiovascular agents, nucleic acids, genetic material, vital vectors, immunoactive agents, imaging agents, immunosuppressive agents, peptides, proteins, physiological gases and gastrointestinal agents.

4. The preparation of claim 2 wherein said at least one bioactive agent is a lipophilic bioactive agent.

5. The preparation of claim 1 wherein said at least one fluorochemical is selected from the group consisting of perfluoroalkanes, fluorinated cyclic compounds, halogenated fluorochemicals, fluorinated alkenes, fluorinated ethers, fluorinated polyethers, fluorinated amines, fluorinated hydrides and derivatives thereof.

6. The preparation of claim 1 wherein said at least one hydrocarbon-based oil is selected from the group consisting of saturated hydrocarbons, unsaturated hydrocarbons, lipids, triglycerides, natural oils, synthetic oils and derivatives thereof, said natural oils selected from the group consisting of canola oil, soybean oil, olive oil, corn oil, castor oil, sunflower oil, safflower oil and derivatives thereof.

7. The preparation of claim 1 wherein said at least one fluorophilic dispersing agent is selected from the group consisting of fluorinated surfactants, fluorocarbon-hydrocarbon diblock compounds and combinations thereof.

8. The preparation of claim 7 wherein said at least one fluorophilic dispersing agent is a diblock compound, said diblock compound having the formula:

$R_F$-L-$R_H$-Z wherein:

$R_F$ is one or more perfluorinated or partially fluorinated group(s);

$R_H$ is one or more hydrocarbon group(s);

L is a linkage unit; and

Z is H or a group more polar or polarizable than the $R_H$.

9. The preparation of claim 7 wherein said fluorophilic dispersing agent is a diblock compound selected from the group consisting of compounds having the formula $C_nF_{2n+1}C_mH_{2m+1}$, compounds having the formula $C_nF_{2n+1}C_mH_{2m-1}$ and combinations thereof, wherein n is an integer from 2 to 12 and m is an integer from 2 to 16.

10. The preparation of claim 7 wherein said fluorophilic dispersing agent is a fluorinated surfactant selected from the group, consisting of compounds having the formula $R_FR_1OP(O)[N(CH_2CH_2)_2O_2]$ compounds having the formula $[R_FR_{1O}]_2P(O)[N(CH_2CH_2)_2O]$ and combinations thereof wherein $R_F$ is $CF_3(CF_2)_t$ such that t is an integer from 1 to 11 and $R_1$ is a substituted or unsubstituted, saturated or unsaturated hydrocarbon chain and wherein both $R_F$ and $R_1$ may contain at least one oxygen and/or sulfur atom.

11. The preparation of claim 1 further comprising at least one bioactive agent.

12. The preparation of claim 11 further comprising one or more additives selected from the group consisting of co-solvents, co-surfactants, co-dispersants, buffers, stabilizers, nutritive agents and combinations thereof.

13. A hydrocarbon-based oil-in-fluorochemical-in-polar liquid multiple emulsion comprising:
   an emulsified disperse phase comprising at least one hydrocarbon-based oil, at least one fluorochemical and at least one fluorophilic dispersing agent wherein said emulsified disperse phase comprises a discontinuous hydrocarbon-based oil phase; and
   a continuous phase comprising at least one polar liquid having at least one emulsifying agent dispersed therein.

14. The multiple emulsion of claim 13 wherein said hydrocarbon-based oil comprises at least one bioactive agent.

15. The multiple emulsion of claim 14 wherein said at least one bioactive agent is a lipophilic bioactive agent.

16. The multiple emulsion of claim 13 wherein said at least one bioactive agent is selected from the group consisting of respiratory agents, antibiotics, antivirals, mydriatics, antiglaucomas, anti-inflammatories, antihistaminics, antineoplastics, anesthetics, ophthalmic agents, enzymes, cardiovascular agents, nucleic acids, genetic material, viral vectors, immunoactive agents, imaging agents, immunosuppressive agents, peptides, promins, physiological gases and gastrointestinal agents.

17. The multiple emulsion of claim 13 further comprising one or more additives selected from the group consisting of co-solvents, co-surfactants, co- dispersants, mineral salts, buffers, stabilizers, oncotic agents, osmotic agents, nutritive agents and combinations thereof.

18. The multiple emulsion of claim 13 wherein said at least one fluorochemical is selected from the group consisting of halogenated fluorochemicals, fluorinated cyclic compounds, perfluoroalkanes, fluorinated alkenes, fluorinated ethers, fluorinated polyethers, fluorinated amines, fluorinated hydrides and combinations thereof.

19. The multiple emulsion of claim 13 wherein said at least one hydrocarbon-based oil is selected from the group consisting of saturated hydrocarbons, unsaturated hydrocarbons, lipids, triglycerides, natural oils, synthetic oils and derivatives thereof, said natural oils selected from the group consisting of canola oil, soybean oil, olive oil, corn oil, castor oil, sunflower oil, safflower oil and derivatives thereof.

20. The multiple emulsion of claim 13 wherein said at least one fluorophilic dispersing agent is selected from the group consisting of fluorinated surfactants, fluorocarbon-hydrocarbon diblock compounds and combinations thereof.

21. The multiple emulsion of claim 20 wherein said at least one fluorophilic dispersing agent is a diblock compound, said diblock compound having the formula:

$R_F\text{-L-}R_H\text{-Z}$ wherein:

$R_F$ is one or more perfluorinated or partially fluorinated group(s);

$R_H$ is one or more hydrocarbon group(s);

L is a linkage unit; and

Z is H or a group more polar or polarizable than the $R_H$.

22. The multiple emulsion of claim 21 wherein said fluorophilic dispersing agent is a diblock compound selected from the group consisting of compounds having the formula $C_nF_{2n+1}C_mH_{2m+1}$, compounds having the formula $C_nF_{2n+1}C_mH_{2m-1}$ and combinations thereof, wherein n is an integer from 2 to 12 and m is an integer from 2 to 16.

23. The multiple emulsion of claim 20 wherein said fluorophilic dispersing agent is a fluorinated surfactant selected from the group consisting of compounds having the formula $R_FR_1OP(O)[N(CH_2CH_2)_2O]_2$ compounds having the formula $[R_FR_1O]_2P(O)[N(CH_2CH_2)_2O]$ and combinations thereof wherein $R_F$ is $CF_3(CF_2)_t$, such that t is an integer from 1 to 11 and $R_1$ is a substituted or unsubstituted, saturated or unsaturated hydrocarbon chain and wherein both $R_F$ and $R_1$ may contain at least one oxygen and/or sulfur atom.

24. The multiple emulsion of claim 13 further comprising at least one bioactive agent.

25. A method for forming a hydrocarbon-based oil-in-fluorochemical dispersion comprising the steps of:

combining at least one hydrocarbon-based oil with an effective dispersing amount of at least one fluorophilic dispersing agent and at least one fluorochemical to provide a dispersion preparation comprising a discontinuous hydrocarbon-based oil phase; and admixing said dispersion preparation to produce a hydrocarbon-based oil-in-fluorochemical dispersion.

26. The method of claim 25 wherein said at least one hydrocarbon-based oil comprises a bioactive agent.

27. The method of claim 25 further comprising the step of mixing said hydrocarbon-based oil-in-fluorochemical dispersion with a polar liquid phase comprising at least one polar liquid and at least one emulsifying agent to provide a multiple emulsion.

28. A dispersion prepared according to the method of claim 25.

29. A dispersion prepared according to the method of claim 26.

30. A method for preparing a hydrocarbon-based oil-in-fluorochemical multiple emulsion comprising the steps of:

combining at least one hydrocarbon-based oil with an effective dispersing amount of at least one fluorophilic dispersing agent, at least one fluorochemical, at least one polar liquid and at least one emulsifying agent to provide a multiple emulsion preparation; and admixing said emulsion preparation to form a multiple emulsion comprising an hydrocarbon-based oil-in-fluorochemical disperse phase and a polar liquid continuous phase.

31. The method of claim 30 comprising the step of incorporating at least one bioactive agent in said emulsion preparation.

32. The method of claim 31 wherein said at least one hydrocarbon-based oil comprises said at least one bioactive agent.

33. A multiple emulsion prepared according to the method of claim 30.

34. A multiple emulsion prepared according to the method of claim 31.

35. A method for delivering a bioactive agent to a patient comprising:

providing a bioactive preparation comprising a hydrocarbon-based oil-in-fluorochemical dispersion and at least one bioactive agent wherein said hydrocarbon-based oil-in-fluorochemical dispersion comprises an effective dispersing amount of at least one fluorophilic dispersing agent; and administering said bioactive preparation to a patient.

36. The method of claim 35 wherein said at least one bioactive agent is selected from the group consisting of respiratory agents, antibiotics, antivirals, mydriatics, antiglaucomas, anti-inflammatories, antihistaminics, antineoplastics, anesthetics, ophthalmic agents, enzymes, cardiovascular agents, nucleic acids, genetic material, viral vectors, immunoactive agents, imaging agents, immunosuppressive agents, peptides, proteins, physiological gases and gastrointestinal agents.

37. The method of claim 35, wherein said bioactive preparation is administered to a patient using a route of administration selected from the group consisting of topical, subcutaneous, pulmonary, intravenous, intraarterial, sinovial, intramuscular, intraperitoneal, nasal, vaginal, rectal, aural, oral and ocular routes.

38. The method of claim 35 wherein said bioactive preparation comprises a hydrocarbon-based oil-in-fluorochemical dispersion.

39. The method of claim 38 wherein said at least one hydrocarbon-based oil comprises a bioactive agent.

40. The method of claim 35 wherein said bioactive preparation comprises a hydrocarbon-based oil-in-fluorochemical-in-polar liquid multiple emulsion, said multiple emulsion comprising an emulsified hydrocarbon-based oil-in-fluorochemical dispersion comprising at least one hydrocarbon-based oil, at least one fluorochemical and at least one fluorophilic dispersing agent and a continuous phase comprising at least one polar liquid having at least one hydrophilic emulsifying agent dispersed therein.

41. The method of claim 40 wherein said at least one hydrocarbon-based oil comprises a bioactive agent.

* * * * *

UNITED STATES PATENT AND TRADEMARK OFFICE
CERTIFICATE OF CORRECTION

PATENT NO. : 5,733,526
DATED : March 31, 1998
INVENTOR(S) : Trevino, et. al.

It is certified that error appears in the above-identified patent and that said Letters Patent is hereby corrected as shown below:

Column 23, line 37, please change "antivitals" to --antivirals--.

Column 23, line 40, please change "vital vectors" to --viral vectors--.

Column 24, line 18, after "$CH_2)_2$" please change "$O_2]$" to --$O]_2$--.

Column 24, line 19, please change "$[R_FR_{10]2}$" to --$[R_FR_1O]_2$--.

Column 24, line 52, please change "promins" to --proteins--.

Column 26, line 50, please change "a bioactive" to --said bioactive--.

Column 26, line 54, please change "an emulsified hydrocarbon" to --said hydrocarbon--.

Column 26, line 61, please change "a bioactive" to --said bioactive--.

Signed and Sealed this

Twenty-fourth Day of October, 2000

Q. TODD DICKINSON

*Attest:*

*Attesting Officer*         *Director of Patents and Trademarks*